US006201872B1

(12) United States Patent
Hersh et al.

(10) Patent No.: US 6,201,872 B1
(45) **Date of Patent: *Mar. 13, 2001**

(54) ACTIVE CONTROL SOURCE CANCELLATION AND ACTIVE CONTROL HELMHOLTZ RESONATOR ABSORPTION OF AXIAL FAN ROTOR-STATOR INTERACTION NOISE

(75) Inventors: Alan S. Hersh, Calabasas; Bruce E. Walker, Westlake Village, both of CA (US); Larry Heidelberg, Lakewood, OH (US)

(73) Assignee: Hersh Acoustical Engineering, Inc., Westlake Village, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/843,542

(22) Filed: Apr. 18, 1997

Related U.S. Application Data

(63) Continuation of application No. 08/762,609, filed on Dec. 9, 1996.
(60) Provisional application No. 60/008,759, filed on Mar. 12, 1995.

(51) Int. Cl.[7] ...................... A61F 11/06
(52) U.S. Cl. ...................... 381/71.5; 381/71.7
(58) Field of Search ...................... 381/71.5, 71.1, 381/71.7, 71.8, 71.14, 338, 337, 353; 415/119; 181/210, 224

(56) References Cited

U.S. PATENT DOCUMENTS 3,936,606 2/1976 Wanke .
4,044,203 8/1977 Swinbanks .
4,109,108 8/1978 Coxon et al. .
4,122,303 10/1978 Chaplin et al. .
4,372,110 2/1983 Cheng .

(List continued on next page.)

OTHER PUBLICATIONS

"Active Noise Cancellation In Ducts In The Presence Of Higher Order Modes", Goodman et al., Digisonix, Inc.
"Active Cancellation Of Higher Order Modes In A Duct Using Recursively–Coupled Multi–Channel Adaptive Control System", Rubenstein et al., Inter–Noise, Jul. 1992.
"Number Of Error Microphones For Multi–Modal Cancellation", Baumann et al., Inter–Noise, Jul. 1992.
"Active Adaptive Sound Control In A Duct: A Computer Simulation", Burgess, J. Acoust. Soc. Am. 70(3), Sep. 1981.
"Active Systems For Sound Attenuation In Ducts", Tichy, IEEE 1988.
"Development Of The Filtered–U Algorithm For Active Noise Control", Eriksson, J. Acoust. Soc. Am. 89(1), Jan. 1991.

*Primary Examiner*—Vivian Chang
(74) *Attorney, Agent, or Firm*—Blakeley, Sokoloff, Taylor & Zafman LLP

(57) ABSTRACT

The present invention is an active-control system for attenuating noise in a duct having a fluid flow. An array of stators having a longitudinal length is positioned axially within the duct. A first array of sound sources capable of generating spinning mode sound and is positioned a distance upstream of a first plane defined by the upstream-most portion of the stators, relative to the fluid flow. The upstream distance is less than the longitudinal length of the stators. A second array of sound sources capable of generating spinning mode sound and is positioned a distance downstream of a second plane defined by the downstream-most portion of the stators, relative to the fluid flow. The downstream distance is less than the longitudinal length of the stators. A controller causes the first and second arrays of sound sources to generate sound including spinning mode sound such that it cancels a portion of the noise within the fluid flow that passes through the stators.

17 Claims, 31 Drawing Sheets

U.S. PATENT DOCUMENTS

| | | | |
|---|---|---|---|
| 4,473,906 | 9/1984 | Warnaka et al. . | |
| 4,589,133 | 5/1986 | Swinbanks . | |
| 4,669,122 | 5/1987 | Swinbanks . | |
| 4,677,676 | 6/1987 | Eriksson . | |
| 4,677,677 | 6/1987 | Eriksson . | |
| 4,965,832 | 10/1990 | Edwards et al. . | |
| 5,018,202 | 5/1991 | Takahashi et al. . | |
| 5,060,271 | 10/1991 | Geddes . | |
| 5,088,575 | 2/1992 | Eriksson . | |
| 5,097,923 | 3/1992 | Ziegler et al. . | |
| 5,119,427 | 6/1992 | Hersh et al. . | |
| 5,146,505 | 9/1992 | Pfaff et al. . | |
| 5,172,416 | 12/1992 | Allie et al. . | |
| 5,478,199 | * 12/1995 | Gliebe | 381/71.5 |
| 5,584,447 | * 12/1996 | Pla | 381/71.5 |

* cited by examiner

— log Amplitude Ratio - nepers

— Phase Difference - radians

ACTIVE CONTROL SOURCE CANCELLATION AND ACTIVE CONTROL HELMHOLTZ RESONATOR ABSORPTION OF AXIAL FAN ROTOR-STATOR INTERACTION NOISE

CROSS-REFERENCE TO RELATED APPLICATIONS

This application is a continuation of U.S. application Ser. No. 08/762,609 filed Dec. 9, 1996, which claims benefit of U.S. Provisional application Ser. No. 60/008,759 filed Mar. 12, 1995.

BACKGROUND OF THE INVENTION

1. Field of the Invention

This invention relates to the field of active control of axial fan rotor-stator interaction noise.

2. Prior Art

Communities located adjacent to commercial airports are often exposed to excessive and annoying noise generated from landing, takeoff and flyover maneuvers. FIG. 1 is a schematic cross-section of the most common propulsion system used in commercial high-bypass-ratio turbofan engines (see *Turbomachinery Noise,* Groeneweg, J. F., Sofrin, T. G. and Rice, E. J., NASA Reference Publication 1258, Vol. 1, WDRC Technical Report 90–3052, August 1991). The various internal noise sources are identified as well as locations of passive sound absorbing treatment. FIG. 2 displays predicted flyover maximum perceived noise levels generated from separate engine components of a typical commercial turbofan engine (taken from *Energy Efficient Engine Propulsion System-Aircraft Integration Evaluation,* Owens, R. E., NASA CR-159488, 1979). Observe that for this engine, the maximum perceived noise levels are dominated by fan inlet and exhaust sources. FIG. 3 displays sound power spectra generated from typical turbomachinery operating at subsonic and supersonic tip speeds. At subsonic tip speeds, large tones are observed at harmonics of the rotor blade-passage frequencies (BPF) in contrast to the spectra at supersonic tip speeds where very large number of tones are generated from rotating shock waves and associated nonlinearities at frequencies both above and below the engine blade passing frequency (BPF).

Despite many years of intensive research, jet engine noise remains as one of the major pollution problems facing communities located near civilian airports. This is not surprising because the suppression of jet engine noise is inherently complex, involving the interaction between different physical phenomena such as (1) complicated radial and spinning modes convecting in three-dimensional flows containing transverse velocity and thermal gradients which refract the sound, (2) subsonic and supersonic accelerating mean flows, (3) combustion noise, (4) acoustic wave propagation and resonance and (5) natural or forced hydrodynamic and acoustic instabilities. As a consequence of the complexity of these mechanisms and their (nonlinear) interactions, very few "practical" guidelines have evolved to allow the engine designer to predict, let alone control, jet noise inlet and exhaust noise in a given design.

The need to improve aircraft performance and efficiency while decreasing community noise taxes the acoustic suppression capability of the sound absorbing treatment that line the ducts of turbofan engines. New ultra-high-bypass engines with shorter inlet and exhaust ducts have less room for acoustic treatment. Thus, more effective treatment is required than is currently available. Much of the treatment used currently has a very limited frequency range over which it is effective, that is, it is only effective for an single tone. If the treatment could be effective for several or all tones at the same time, than all of the treatment area would be available for each tone.

Active sound attenuation is a relatively old concept that has received considerable attention in recent years, primarily because the increasing availability of fast programmable signal processing hardware has made these systems viable for audio frequency applications. Although active noise control technology has been demonstrated to be very successful in many industrial noise control applications, it has been not been used in applications that are sensitive to the severe weight, size, ruggedness, reliability and energy constraints required in the control of excessive commercial jet engine noise.

BRIEF SUMMARY OF THE INVENTION

The present invention is based on two novel and unique active noise control concepts to achieve significant reduction of the intense rotor-stator interaction tones generated in commercial high bypass turbofan engines and commercial HVAC axial fans. In accordance with the first concept, arrays of active control sound sources are installed on the inlet side (upstream) and on the exhaust side (downstream) of the stator vanes of an axial fan. The sound fields radiated from the fan inlet and exhaust are canceled simultaneously by driving the arrays of active control sound sources with the appropriate amplitude and phase.

The second concept is based upon an active control sound absorption scheme. Arrays of active control Helmholtz resonators are installed between the fan inlet and the rotors of an axial fan to absorb rotor-stator generated tones. The sound fields radiated from the fan inlet are canceled by driving the arrays of active control resonators with the appropriate amplitude and phase. With a duplicate arrangement, the system would be extended to cancel the modes in the exhaust duct as well.

An adaptively controlled dipole sound source system has been tested and shown to provide 29 dB of attenuation in the inlet and 19 dB in the exhaust of the cosine component of the (2 0) rotor-stator interaction tone in axial fan facility. The novelty of the control scheme is that by utilizing knowledge of the mode transmitted in the duct, the complexity of the control algorithm is reduced dramatically. Furthermore, since the system is configured to only generate the desired modes, one can expect superior performance since unwanted plane-waves and other modes will not be generated.

DETAILED DESCRIPTION OF THE INVENTION

Figure 1:
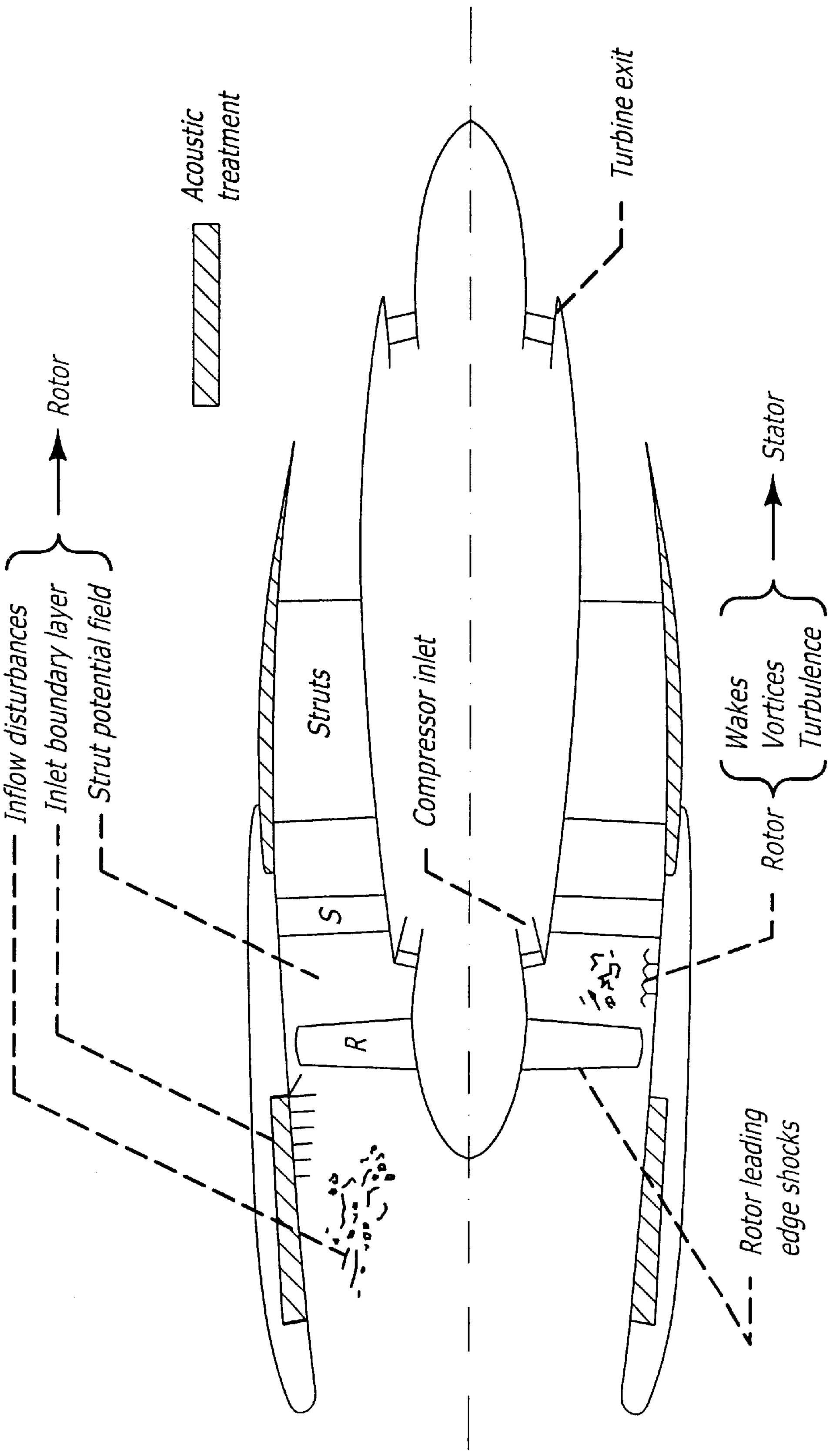
FIG. 1 is a schematic cross-section of the most common propulsion system used in commercial high-bypass-ratio turbofan engines.
Figure 2:
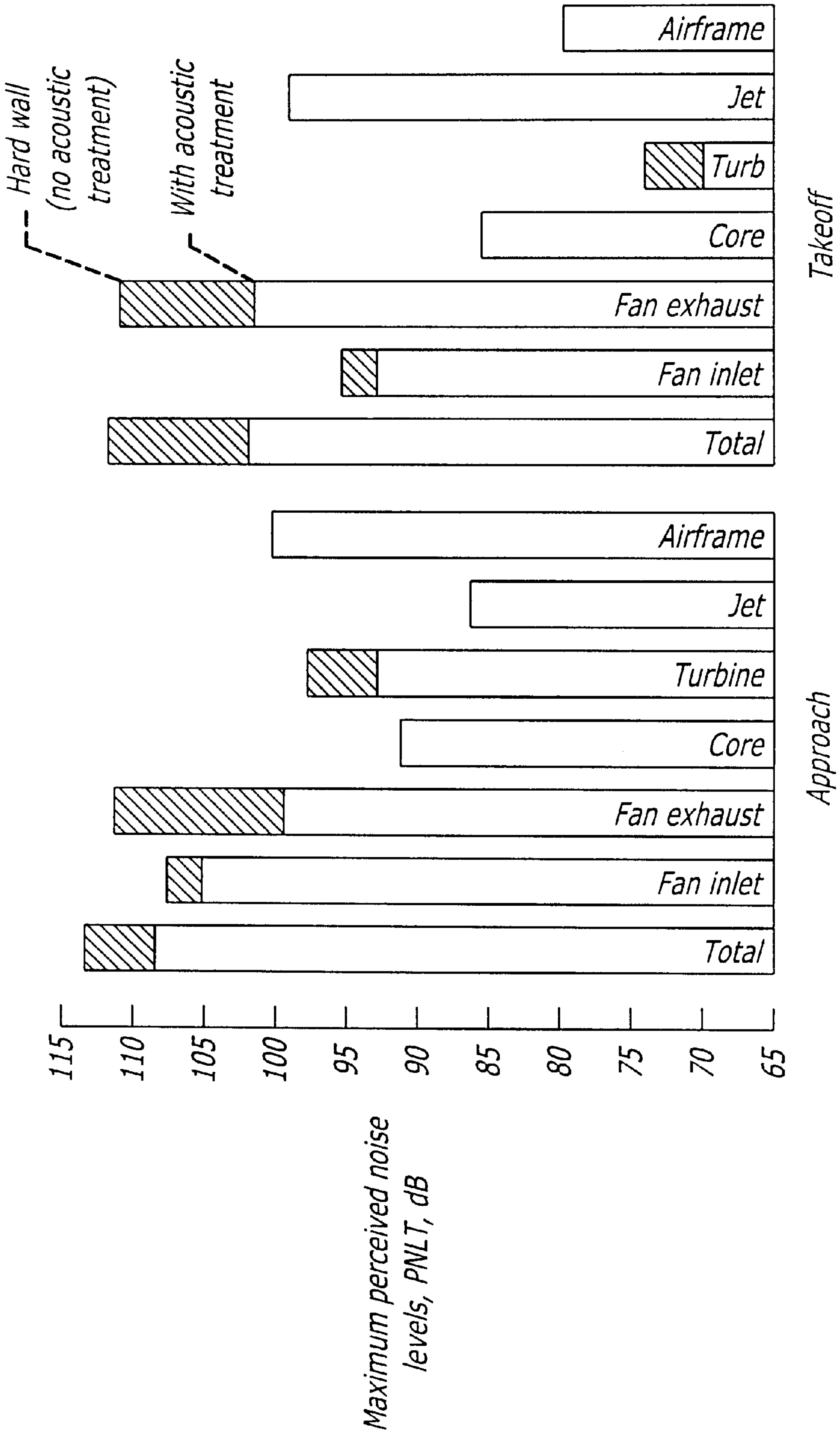
FIG. 2 illustrates the predicted flyover maximum perceived noise levels generated from separate engine components of a typical commercial turbofan engine.
Figure 3A:
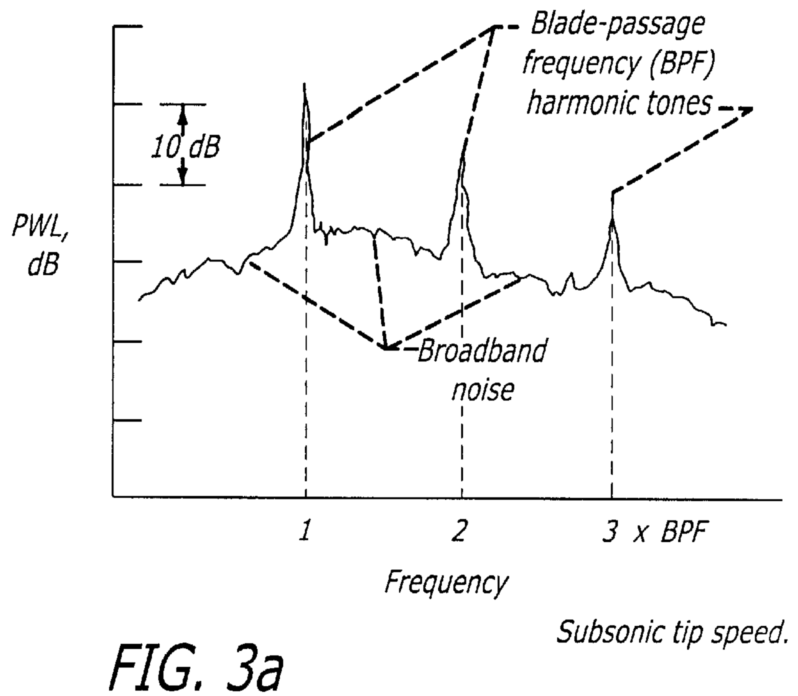
FIG. 3 illustrates the sound power spectra generated from typical turbomachinery operating at subsonic and supersonic tip speeds.
Figure 3B:
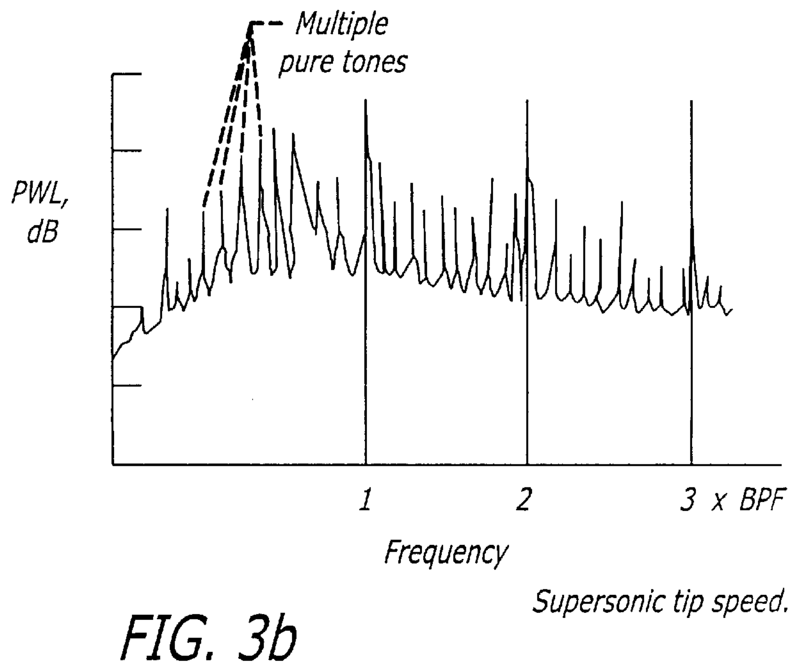
Figure 4:
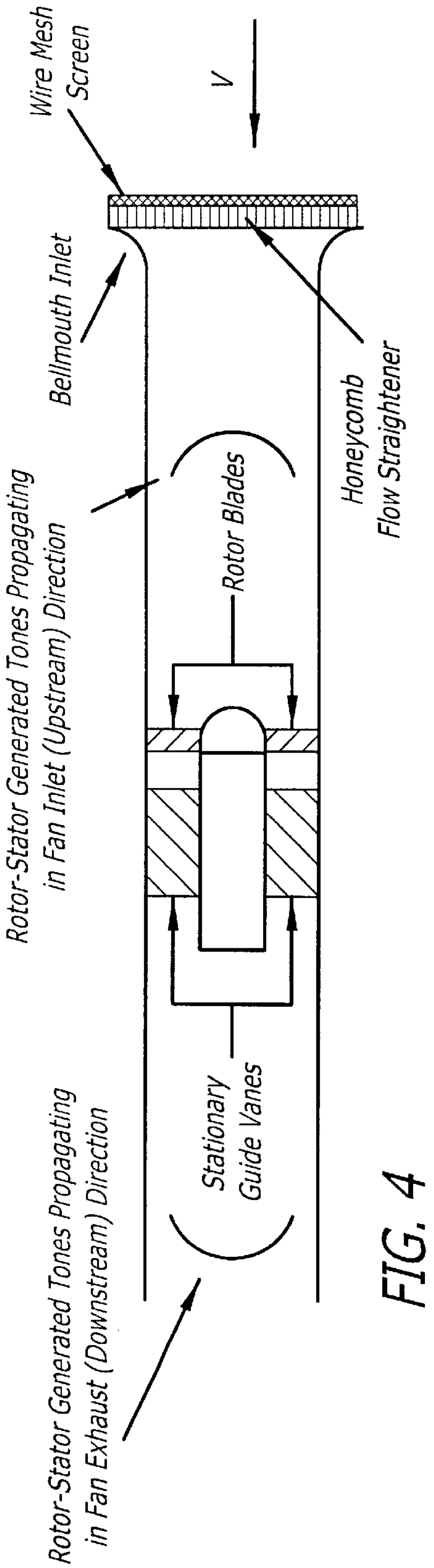
FIG. 4 is a schematic diagram of a generic axial flow fan with rotor-stator interaction noise generation.

The present invention is based on two novel and unique active noise control concepts to achieve significant reduction of the intense rotor-stator interaction tones generated in commercial high bypass turbofan engines and commercial HVAC axial fans. Referring to the axial fan arrangement of FIG. 4, Tyler and Sofrin showed, in their pioneering paper, that rotor-stator tones are generated from the interaction between rotor trailing-edge wakes and downstream stator vanes (*Axial Flow Compressor Noise Studies,* Tyler, J. M. and Sofrin, R. G., Soc. Auto. Engr. Trans., Vol. 70, 309–332, 1962). It is well known that these kinds of interactions generate dipole sound (*Aeroacoustics,* Goldstein, M. E., NASA SP-346, 1974). However, other interactions within the engine may generate monopole and quadrupole sound, depending upon blade thickness, fan tip speed, etc.

Figure 5:
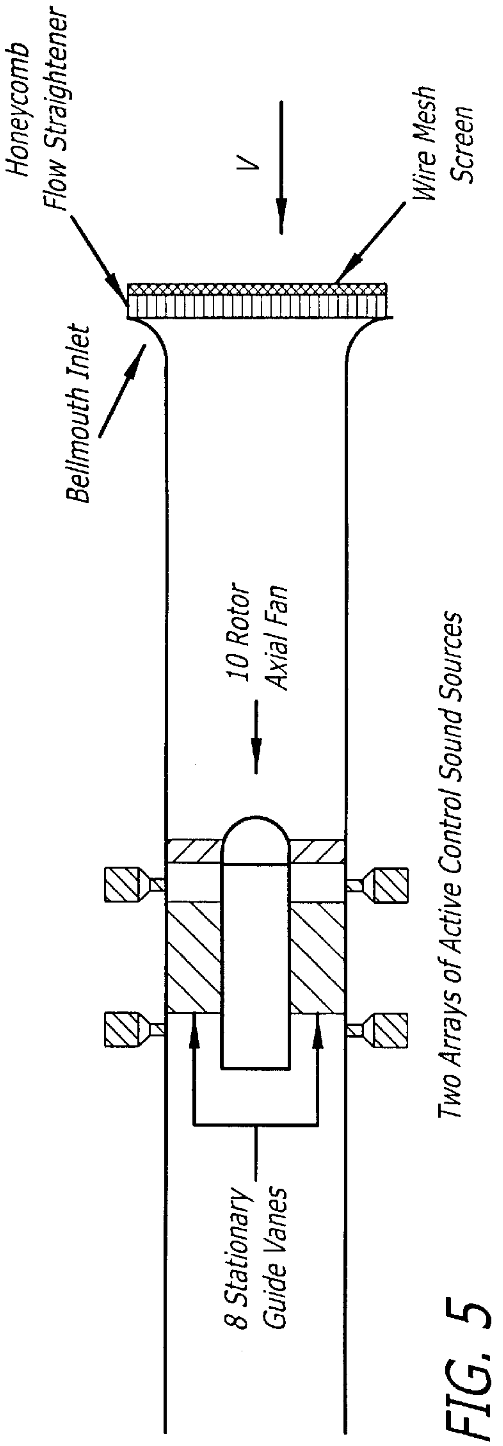
FIG. 5 is a diagram of the active noise source cancellation system of the present invention.

The first concept is based upon the active noise source cancellation system shown schematically in FIG. 5. Arrays of active control sound sources are installed on the inlet side (upstream) and on the exhaust side (downstream) of the stator vanes of an axial fan. The sound fields radiated from the fan inlet and exhaust are canceled by driving the arrays of active control sound sources with the appropriate amplitude and phase.

Figure 6:
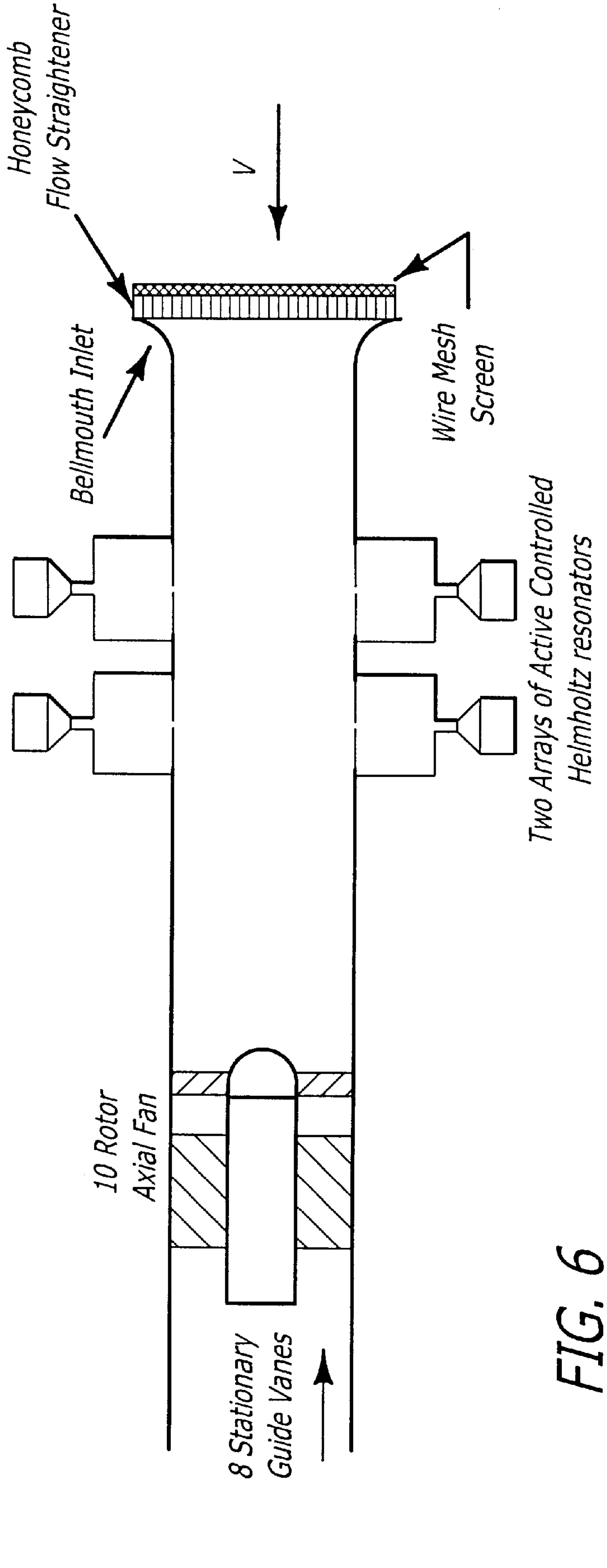
FIG. 6 is a schematic diagram of the active control Helmholtz resonator sound absorption system of the present invention.

The second concept is based upon the active control sound absorption scheme shown schematically in FIG. 6. Arrays of active control Helmholtz resonators are installed between the fan inlet and the rotors of an axial fan to absorb rotor-stator generated tones. The sound fields radiated from the fan inlet are canceled by driving the arrays of active control resonators with the appropriate amplitude and phase. With a duplicate arrangement, the system could be extended to cancel the modes in the exhaust duct as well.

An adaptively controlled dipole sound source system has been tested and shown to provide 29 dB of attenuation in the inlet and 19 dB in the exhaust of the cosine component of the (2 0) rotor-stator interaction tone in axial fan facility. The system is currently configured to cancel the cosine component of a single mode. It is straightforward to extend this system to globally cancel both the sine and cosine components simultaneously of a single mode as well as the global cancellation of multiple modes. This would require an analog system to (1) generate each of the modes from a single sine wave using a multiple-source acoustic array and (2) monitor the microphone array to generate quadrature components for each of the M-modes. In the simplest arrangement in which rotor-stator propagating modes are generated using a linear combination of the microphone signals, there is the implicit assumption of orthogonality of the modes. If this is not the case, the possibility arises of cross-talk between the mode-outputs. One of the major advantages of the present invention is that it will achieve global cancellation of multi-modal sound waves propagating at different frequencies. The scheme breaks down, however, for multi-modal sound waves propagating at the same frequency. Provided the analog hardware is available, the multi-mode system requires one control loop per mode. Each loop would require one output (to drive the analog mode generator) and two inputs for the quadrature components of the modes. In the case where the sum of upstream and downstream power needs to be minimized, there are four rather than two quadrature components per mode.

The novelty of the control scheme is that by utilizing knowledge of the mode transmitted in the duct, the complexity of the control algorithm is reduced dramatically. Furthermore, since the system is configured to only generate the desired mode, one can expect superior performance since unwanted plane-waves and other modes will not be generated.

The description of the present invention is organized as follows. Following this introduction, a detailed description of the test facility, data acquisition scheme, real-time control system and sound attenuation performance of the active control source cancellation is described, followed by the description of the corresponding test facility and sound attenuation performance of the active control resonator.

1. ACTIVE CONTROL SOURCE CANCELLATION INVENTION

Aerodynamic noise sources in fans and other turbomachinery may be comprised of a combination of monopole, dipole and quadrupole components depending upon the rotor-stator thicknesses, rotational speeds, etc. The rotor/stator interaction noise for many commercial high bypass turbofan engines is expected to be primarily dipoles. Radiation toward the inlet and exhaust portions of the duct depends upon the effective orientation of the dipole sources relative to the propagation angle of the excited mode. It is not possible to know in advance whether the inlet and exhaust signals will be in phase or out of phase, or what the relative amplitudes will be in the two directions. These will be dependent upon rotor blade and stator vane geometries, flow speed, BPF, mode number, etc.

Detailed descriptions of the test facility and data acquisition and reduction schemes, real-time control system and sound attenuation performance of the active control source cancellation invention are presented in Sections A–C below.

A. TEST FACILITY AND DATA REDUCTION SCHEME

Figure 7:
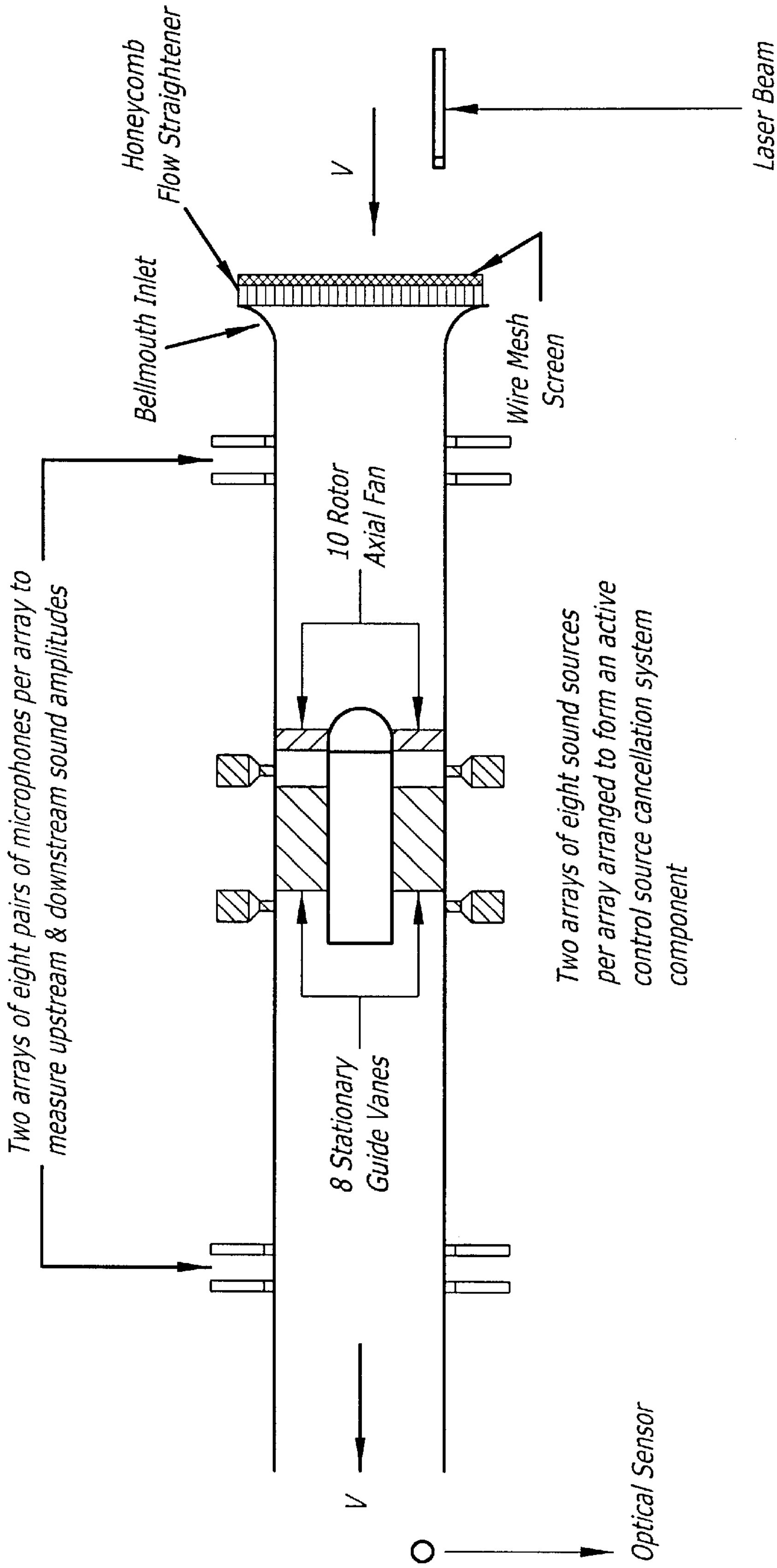
FIG. 7 is a schematic of the Axial Fan Flow Facility used in a laboratory test program to validate the proposed active control source cancellation system of the present invention.

FIG. 7 is a schematic of the Axial Fan Flow Facility used in a laboratory test program to validate the proposed active control source cancellation invention. Starting on the right side, the system components consist of (1) a laser, located upstream of the duct inlet, emitting a beam that passes through the fan and incident on an optical sensor located downstream of the duct exhaust, used to measure rotor speed and to derive a blade passage signal, (2) a wire mesh screen and honeycomb flow straightener attached to a Bell Mouth inlet to stabilize flow disturbances generated principally from inlet ground vortices, (3) two arrays of eight microphones per array, the microphones of each array being spaced circumferentially in 45° increments with each microphone of each array being paired with the correspondingly circumferentially positioned microphone of the other array to measure separately the inlet and exhaust propagating sound pressure fields in the space between the duct inlet and the fan, (4) two arrays of eight sound sources per array spaced upstream and downstream of the stator vanes, the sound sources of each array being distributed in 45° increments around the periphery of the of the duct, (5) a Joy Axial Fan containing a 10 blade rotor and eight stationary guide vanes and (6) two arrays of eight microphones per array, the microphones of each array being spaced circumferentially in 45° increments with each microphone of each array being paired with the correspondingly circumferentially positioned microphone of the other array to measure separately the inlet and exhaust propagating sound pressure fields in the space between the fan and the duct exhaust. A variable speed controller (not shown) was used to vary the fan speed over the range 0–3530 RPM. Table I below defines the basic operating conditions of the Axial Fan Facility shown schematically in FIG. 7.

TABLE I

HAE Axial Fan Operating Parameters

| Description | Symbol | Value |
|---|---|---|
| Duct Diameter | D | 1.98 ft |
| Rotor/Stator Spinning Mode | (m,n) | (2,0) |
| Rotor/Stator Eigenvalue | $\alpha_{2,0}$ | 0.9722 |
| Rotor/Stator Cut-On Frequency | $f_{2,0}$ | 555 Hz |
| Spoiler/Rotor Spinning Mode | (m,n) | (1,0) |
| Spoiler/Rotor Eigenvalue | $\alpha_{1,0}$ | 0.5861 |
| Spoiler/Rotor Cut-On Frequency | $f_{1,0}$ | 338 Hz |
| Mean Flow Velocity | $V\infty$ | 0 & 32–34 ft/sec |

Figure 8:
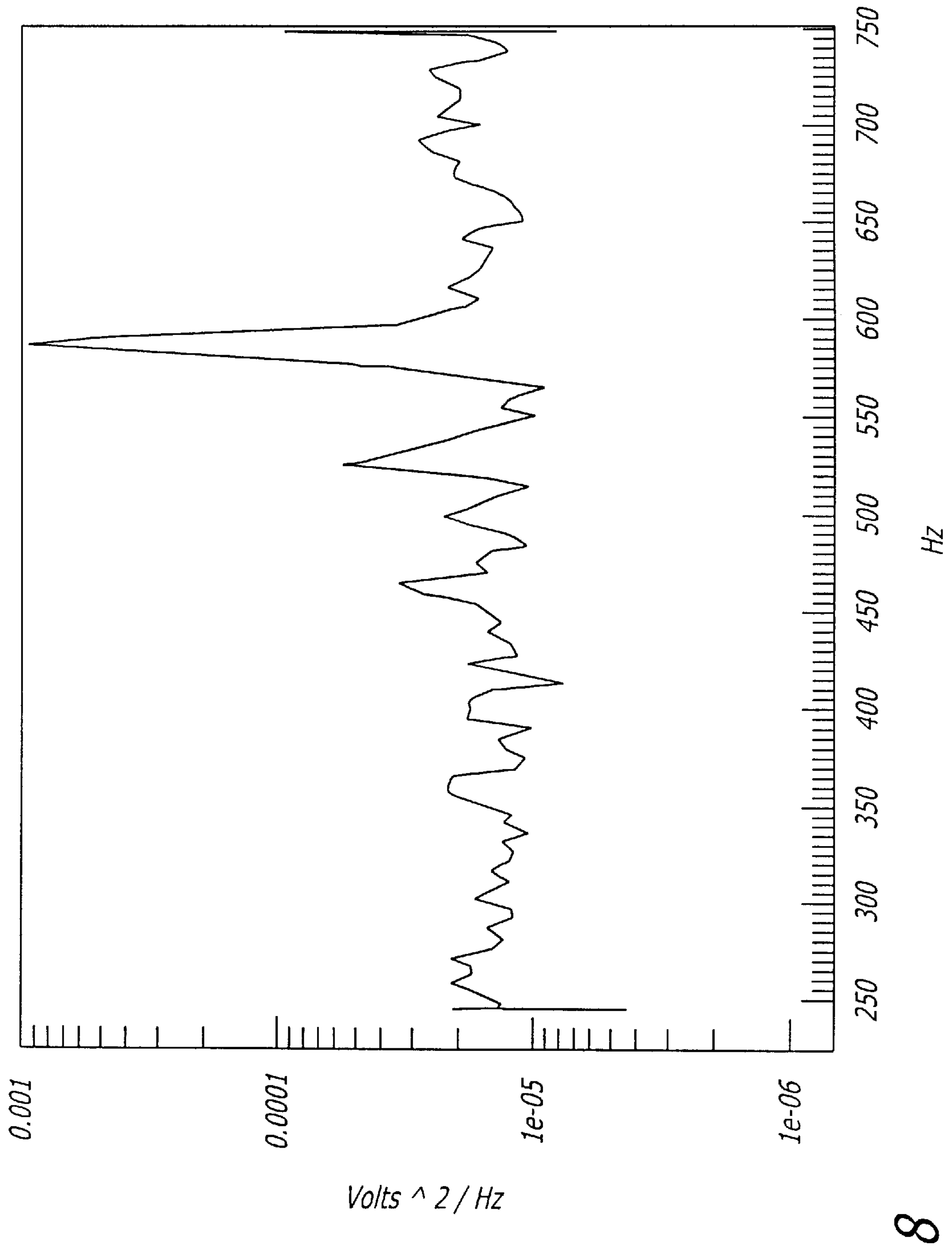
FIG. 8 illustrates the power spectral measurements (PSD) of the sound pressure radiated from the inlet of a fan 24-inch diameter duct.

The sound fields in cylindrical ducts, when excited by rotor/stator interactions in axial-flow fans, take the form of "spinning modes" with frequency an integer multiple of the number of rotor blades B times the rotational speed Ω and tangential wave number m as derived by Tyler-Sofrin (*Axial Flow Compressor Noise Studies, supra):*

$$m=nB+pV,\ p=\ldots,-1,0,1,\ldots \tag{1}$$

where n is the harmonic number or multiple of the blade fundamental rotational frequency (BPF≡BΩ/2π) and V is the number of stator vanes (or spoiler rods). Applying Eq. (1) to the axial fan shown schematically in FIG. 7, the (2,0) mode is generated at the blade passing rate (n=1) for p=−1. For the fan 24-inch diameter duct, the cut-on frequency of the (2,0) spinning mode at normal room temperatures is about 550 Hz. The (2,0) mode will become a significant noise control issue for fan speeds of 3300 RPM and higher. This was confirmed by the power spectral measurements (PSD) of the sound pressure radiated from the inlet shown in FIG. 8. These measurements were recorded at a fan speed of 3517 RPM which corresponds to a frequency of 586 Hz, well above the (2,0) mode cut-on frequency of 550 Hz.

For each tangential wave number, an infinite number of radial "modes" is possible. Typically, the indices (m,n) are used to denote the tangential wave number ("lobes") and number of radial nodes, respectively, in a given cylindrical mode. For both cylindrical and annular ducts, (m,n) defines a cut-on frequency, inversely proportional to the physical dimensions of the duct, above which the duct will support acoustic propagation and below which, sound will decay exponentially. For each (m,n) mode, the downstream propagating sound field $P_{mn}$ in an infinite cylindrical duct may be written as:

$$P_{mn}(r,\theta,z,t)=J_m\left(\frac{\pi\alpha_{mn}r}{R}\right)e^{i(\omega t-m\theta-k_z z)} \tag{2}$$

where (r,θ,z,t) represents the location within the duct at time t, $J_m$ is the Bessel function of order m, m and n represent the sound pressure circumferential and radial mode indices respectively, $k_z$ is the sound wave axial component, (ω=2πf) is the radian frequency, R is the duct radius and $\alpha_{mn}$ is the sound pressure eigenvalue.

For purposes of measurement with stationary microphone arrays and control with stationary transducers, it proves to be convenient to recast the θ dependence as a superposition of two stationary waves cos(mθ) and sin(mθ) using the identity:

$$e^{im\theta} = \cos(m\theta) + i\sin(m\theta) \tag{3}$$

Thus, a "spinning mode" is equivalent to a cosine oriented stationary wave and a sine oriented stationary wave excited simultaneously with equal amplitude, the latter with a phase shift of π/2 or 90° with respect to the former. If the amplitudes of the sine and cosine components are unequal or if the relative phase is not equal to + or −90°, then the result is a combination of stationary and spinning waves.

Microphone Array Considerations

Figure 9:
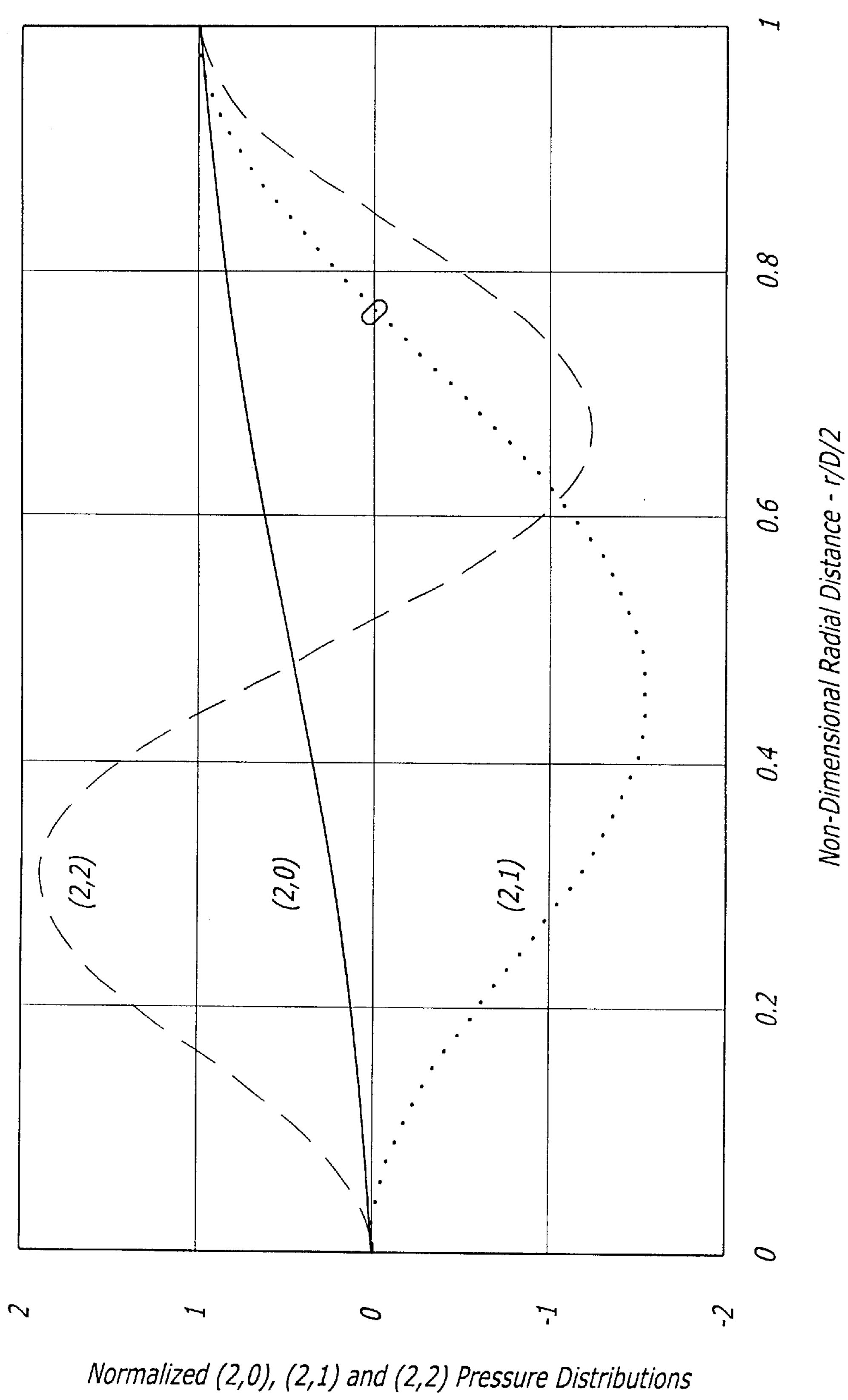
FIG. 9 shows the radial pressure distribution for the (2,0), (2,1) and (2,2) modes, normalized so that the amplitudes are equal at the duct wall.

The sound pressure detection system represents an essential element in the validation of the concept. In order to measure the sound field, it is necessary to use an array of sensors to identify or separate the various spinning and/or stationary propagation modes which may be present in the duct. The orthogonal property of the wave equation solutions in the azimuthal direction allows modes to be separated by performing "spatial Fourier transforms" of signals from uniform sampling positions in the directions of interest (r,θ). Because of the non-periodic behavior of the Bessel functions which define the radial pressure distribution, mode separation with uniformly spaced microphones is not as straightforward as is the separation in the azimuthal direction. FIG. 9 shows the radial pressure distribution for the (2,0), (2,1) and (2,2) modes, normalized so that the amplitudes are equal at the duct wall. The orthogonal property provides that $$\int_0^R [P_{m,n}(r)P_{m,n\neq n}(r)]r\,dr = 0 \tag{4}$$

so that mode separation is possible in principle. Therefore, if microphones are spaced radially so that they "straddle" nodal diameters for all modes to be recovered, linear algebra provides the coefficients for mode separation matrices. Except for separation of (0,n) modes, microphone location at the center of the duct is of no use, as the pressure for the case m≠0 is zero at the center. For separation of modes (m, 0) and (m, 1), two arrays, one at R and the other at approximately R/2 provide the required signals. For separation of modes (m, 0) through (m,2), three radially spaced arrays are required, etc.

In a real application with high speed flow present, microphones at locations other than flush mounted in the walls of the duct are not feasible. However, the dispersive propagation properties of the m,n order spinning modes may be exploited to separate two or more n-order modes at a common m-order. In particular, spacing two circumferential arrays one-half wavelength axially for a particular n-order mode will suppress response to that mode. Alternatively, multiple circumferential arrays may be used with "beam-steering" signal processing to selectively respond to individual modes and reject others.

As with any discrete sampling system, the Nyquist criterion applies and the highest mode number which can be identified, without aliasing, is one-half the number of microphones in the sensor array. In order to resolve the cosine and sine modes of up to order m, the number of microphones, spaced equally around the circumference of the duct, must be greater than 2m+1 times the number of radial modes to be resolved.

A potential disadvantage to using the minimum number of microphones for the m-order mode separation array $(2m_{max}+1)$ is that there is minimal protection against aliasing of higher modes. In systems where most acoustical excitation is at frequencies below which these modes would be cut-on, the problem would be minimal. However, it must be noted that with five microphones, the m=3 and m=2 modes would be indistinguishable. The research/demonstration facility uses eight microphones per array, so that the first aliased mode is m=5.

Figure 10A:
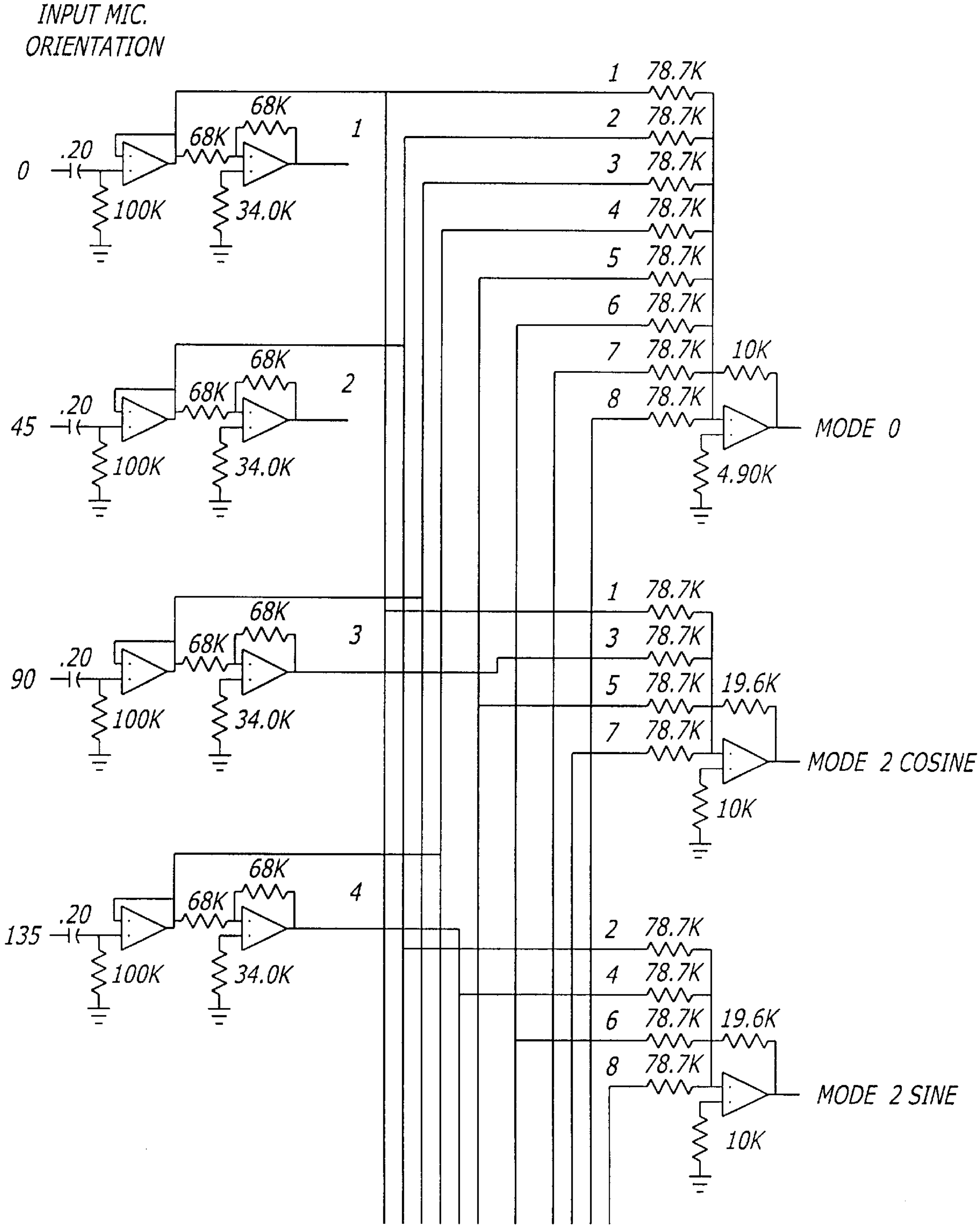
FIG. 10 shows a typical summing amplifier circuit, in which the conductances of the summing resistors are proportional to the mode position coefficients.
Figure 10B:
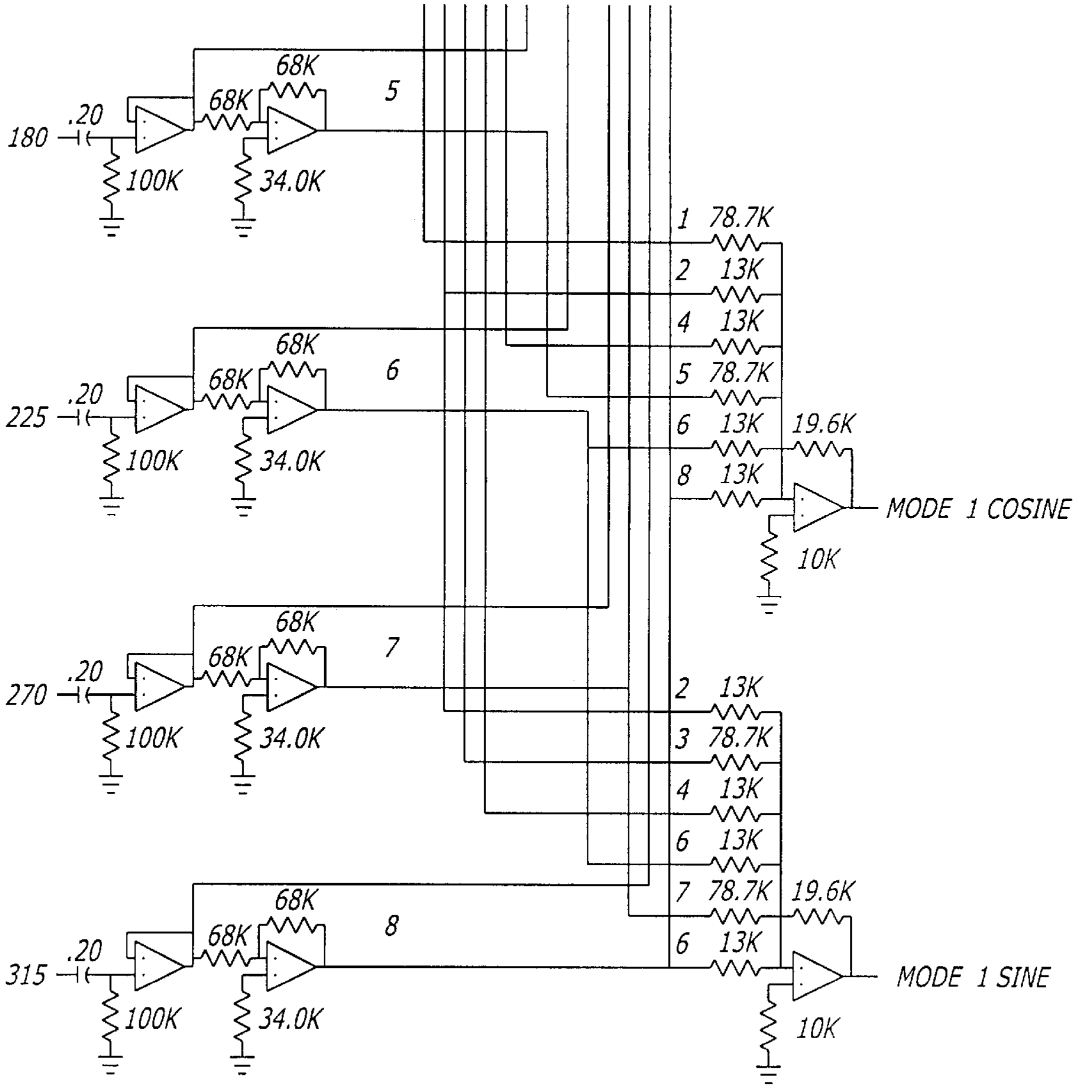

Referring to FIG. 7, and as discussed previously, two arrays of eight pairs of microphones, spaced 45° circumferentially, were installed in the duct as shown. The spatial transforms may be accomplished by summing the outputs of the array microphones, which have been pre-weighted by the appropriate sine, cosine and Bessel function position coefficients. FIG. 10 shows a typical summing amplifier circuit, in which the conductances of the summing resistors are proportional to the mode position coefficients. The microphone signals were connected to an analog signal processing matrix which, for each annular array separates the received signals into plane-wave, first-order sine and cosine and second-order sine and cosine propagation modes. For purposes of this experiment, only the two second-order mode signals were used, following verification that the plane-wave mode was not significant above 550 Hz.

Wave Propagation Direction Separation

The separation of the total acoustic signal at a given axial location into (0, 0), (1, 0) and (2, 0) cylindrical mode components is accomplished with arrays of eight microphones spaced 45° around the circumference of the duct and mode separation matrices as described above. Separating these modes into upstream and downstream traveling wave components requires dual arrays, spaced axially. The m-order mode signals from each array/mode separation matrix pair were processed by adding and subtracting the sum and time-integrated difference between the two arrays of the pair.

$$\begin{matrix} P_{left}(z) \\ P_{right}(z) \end{matrix} \cong \frac{P\left(z-\frac{\Delta z}{2}\right)+P\left(z+\frac{\Delta z}{2}\right)}{2} \pm \frac{2\pi f}{k_z\Delta z}\int\left[P\left(z-\frac{\Delta z}{2}\right)-P\left(z+\frac{\Delta z}{2}\right)\right]dt \tag{5}$$

where P(z) is the time-domain pressure signal at axial location z, Δz is the microphone array spacing, f is the frequency and $k_z$ is the axial wavenumber. Thus, with appropriate weighting factors for the microphone spacing and mode axial trace velocity, signals for the two axial directions can be separated in real time.

The above formulation is only approximate due to several factors. First, the second term on the right-hand-side approximates the pressure gradient by the pressure differential. This introduces minimal error if the microphone spacing is one-eighth wavelength or less. Second, it assumes that $k_z$ is the same for both left and right traveling waves. This is true only in the absence of mean flow.

Figure 11:
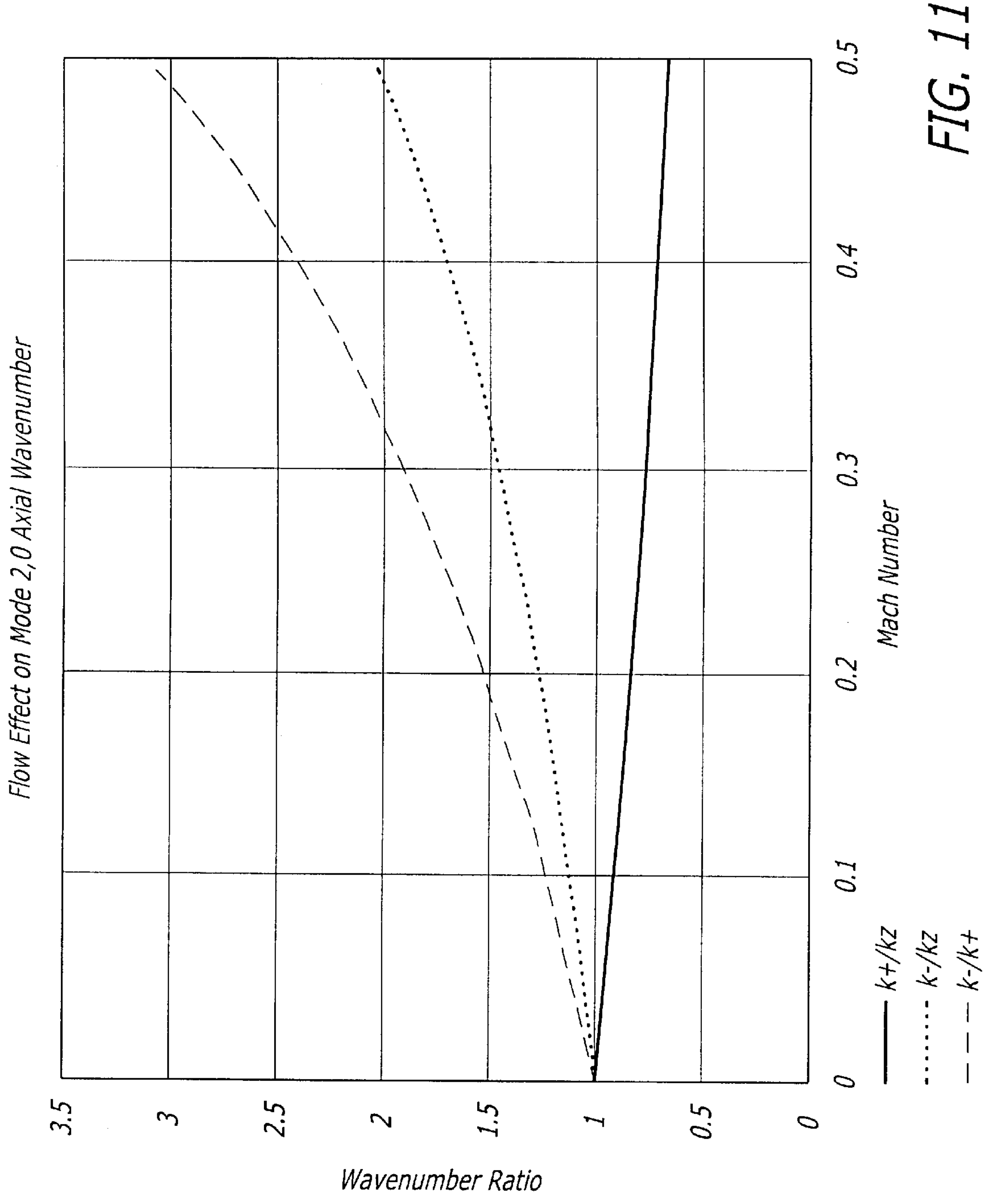
FIG. 11 is an illustration of the ratios of $k_+/k_z$ and $k_-/k_z$ where $k_z$ is the M=0 case.

The axial wave numbers for upstream and downstream propagation, required for a strictly accurate wave separation algorithm are based upon Rice's formulation (*Optimum Wall Impedance for Spinning Modes-A Correlation With Mode Cut-Off Ratio,* Rice, E. J., Journal of Aircraft, Vol. 16, No. 5, May 1979, and *Modal Propagation Angles in Ducts With Soft Walls and Their Connection With Suppressor Performance,* Rice, E. J., NASA-TM-79081). Using Rice's results, the axial wave numbers may be written as $$k_{\pm} = \frac{\sqrt{k^2 - \left(\frac{\alpha_{mn}}{R}\right)^2 (1 - M^2)} \mp kM}{(1 - M^2)} \quad (6)$$

where k=ω/c and M is the mean flow centerline Mach number. FIG. 11 shows the ratios of $k_+/k_z$ and $k_-/k_z$ where kz is the M=0 case.

For more precise measurement of the signals traveling upstream and downstream in the duct, the complex signal components at frequency f may be transformed as follows:

$$P_{left}(f) = \left[\frac{P\left(z+\frac{\Delta z}{2}\right) - P\left(z-\frac{\Delta z}{2}\right)e^{-ik_-\Delta z}}{e^{-ik_+\Delta z} - e^{-ik_-\Delta z}}\right] \quad (7)$$

$$P_{right}(f) = \left[\frac{P\left(z-\frac{\Delta z}{2}\right)e^{-ik_-\Delta z} - P\left(z+\frac{\Delta z}{2}\right)}{e^{-ik_+\Delta z} - e^{-ik_-\Delta z}}\right]$$

The more precise method is useful as a diagnostic tool. However, because it is not a real-time process, it does not afford signals which can be used as "errors" in a rapidly converging adaptive control system. Therefore, the approximate analog wave separation approach was used for the active control tests.

Figure 12:
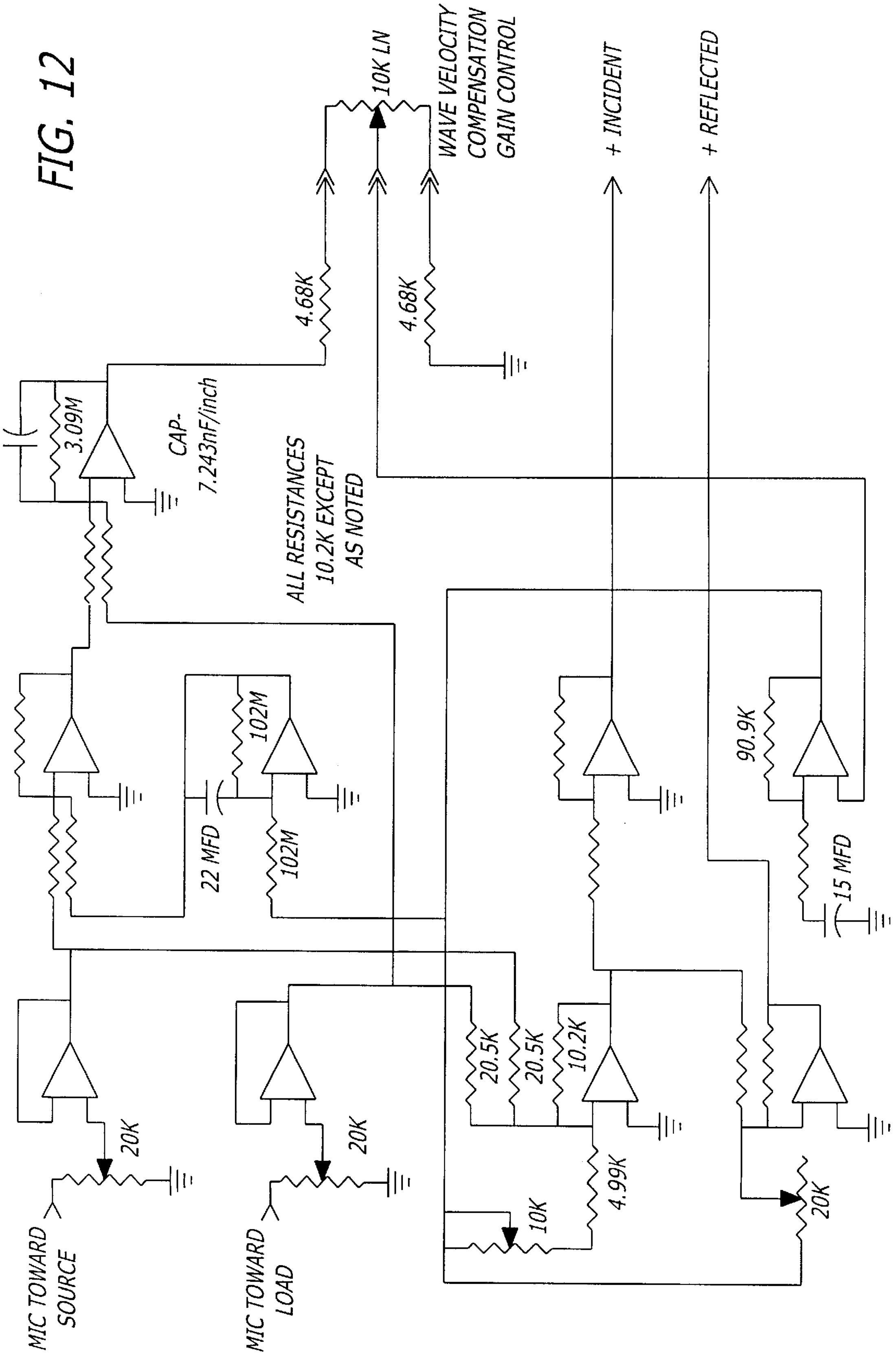
FIG. 12 is a schematic diagram of the circuit used to measure the incident and reflected waves.

FIG. 12 is a block diagram of the circuit used to separate and measure the incident and reflected waves. The microphone mounting blocks were constructed to each accept two Knowles 1751 condenser microphones spaced axially 3-inches, for a total of 32 microphones as shown on FIG. 7. The 32 microphone channels were all calibrated using a Bruel & Kjaer type 4230 acoustic calibrator with a custom prepared adapter plug. Concurrent with the calibration process, the function of the mode separation matrix was verified for each input channel and mode output.

A narrow band signal analyzer (Rion type SA-77 or MassComp Computer) was used to read single mode signals from the mode separation matrix and wave separation processor. The eight signals defined in Table II were measured, FFT analyzed and stored for plotting.

TABLE II

Summary of Array Signals used in FFT Analysis

| Signal # | Array | Signal Mode | Description |
|---|---|---|---|
| 1 | Inlet | 1 cosine | Propagation Toward Inlet |
| 2 | " | 1 sine | " |
| 3 | " | 2 cosine | " |
| 4 | " | 2 sine | " |
| 5 | Exhaust | 1 cosine | Propagation Toward Exhaust |
| 6 | " | 1 sine | " |
| 7 | " | 2 cosine | " |
| 8 | " | 2 sine | |

As discussed previously, cosine and sine refer to arrays for sensing of modes with 0° and 90° orientation in mode-space respectively. The "exhaust array" was located on the exhaust side of the fan for tests of global cancellation using controlled sources flanking the fan. It was located between the fan inlet and the array of controlled sources/active Helmholtz resonators for the tests of inlet sound absorption. In both cases, the "inlet array" was located between the duct inlet and the controlled sources and fan.

In accordance with the Tyler-Sofrin theory, rotor/stator interaction noise produced by the fan is expected to consist of spinning modes of orientation determined by the geometry of the fan. However, in practice, small asymmetries in the fan, inflow or duct elements will result in generation of unexpected modes, including spinning modes of opposite orientation to those predicted. The following discussion describes (1) the software developed to transfer inlet and exhaust sine and cosine stationary sound pressure component measurements into their corresponding clockwise and counter-clockwise spinning components and (2) conducting calibration tests to validate the accuracy of the software.

An algorithm was developed to separate the sine and cosine spatial mode amplitude and phase outputs from the microphone arrays into their clockwise and counter-clockwise spinning wave components. This involved solving the following 4×4 system of transcendental equations, $$A_+\cos(\phi_+) - A_-\cos(\phi_-) = A_{sin}\sin(\phi_{sin})$$

$$A_+\cos(\phi_+) + A_-\cos(\phi_-) = A_{COS}\cos(\phi_{cos})$$

$$A_+\sin(\phi_+) + A_-\sin(\phi_-) = A_{cos}\sin(\phi_{cos}) \quad (9)$$

$$A_+\sin(\phi_+) - A_-\sin(\phi_-) = -A_{sin}\cos(\phi_{sin})$$

where the subscripts "+", "–", "COS" and "sin" are defined in Table III below.

TABLE III

Subscripts Definitions for Equation (9)

| Sub-sript | Definition |
|---|---|
| + | Co-Fan Rotation Direction of Spinning Mode |
| – | Counter-Fan Rotation Direction of Spinning Mode |
| cos | Cosine Stationary Wave Component (Measured) |
| sin | Sine Stationary Wave Component (Measured) |

Equation (9) were solved for each of the measurement cases with $A_+$ and $A_-$ constrained to be equal to or greater than 0.

An initial set of measurements was taken using these wave separation algorithms. The following procedures were used:

1. The axial fan was operated with drive frequencies of 58 to 60 Hz in 0.5 Hz steps resulting in corresponding BPFs of 567 to 587 Hz in 5 Hz steps. The corresponding centerline airflow speeds ranged from 30 to 36 feet/second. Five sets of measurements were taken for each fan speed and solved for spinning wave components. The spinning wave components were then averaged and tabulated.
2. With the fan stationary, one set of measurements was taken with the loudspeaker array driven from a sine wave oscillator and a Hilbert transform processor. Oscillatory frequencies were set to duplicate as closely as possible the fan BPF. These results have also been tabulated.
3. At representative frequencies, the connections to the sine and cosine loudspeaker arrays were switched and it was verified that the direction of the dominant spinning wave was reversed.

B. GLOBAL SOURCE CANCELLATION SCHEME

A computer simulation was conducted to examine the behavior of sound waves generated from a circular array of sources on the perimeter of a cylindrical duct. The analysis starts with the assumption that the source array consisted of eight monopole sound sources arranged in four pairs of dipoles spaced 90° apart, the axes of which are 7.6 cm long and could be rotated through 360°. The signal phase to each dipole was advanced 90° relative to the previous, resulting in excitation of the spinning mode (2,0). For each orientation of the dipoles from 0° to 360°, the amplitude and phase of the transmitted signal was computed for equal distances on either side of the array. The amplitude ratio and phase difference between the "left" and "right" waves were plotted as a function of dipole orientation. The reference orientation (0°) was taken as the case of tangential off-set only (all sources at the same axial location). Thus an orientation of 90° corresponds to axial offset only.

The simulation was first run with no mean flow present. For all test frequencies, the left and right axial-direction waves were equal in amplitude and of the same polarity at dipole rotation angles 0° and 180°, and of equal amplitude and opposite polarity at rotation angles 90° and 270°. In other words, because the actual propagation angle of acoustical energy within the duct is oblique to the duct axis, the dipole source arrays produce monopole-like fields (same polarity upstream and downstream) if the dipole axes are close to tangentially aligned. Similarly, they produce opposite-polarity signals upstream and downstream if dipole axes are near axially aligned.

With flow present, as expected, the acoustic field becomes asymmetric and optimum dipole coupling to the spinning modes occurs at different angles for upstream and downstream waves. For very low flow speeds (M≡0.03) considered in the demonstration program, the changes are relatively small.

Application of these concepts to the dipole source spinning mode cancellation project is clear. Although the aerodynamic sound sources associated with the rotor-stator interaction are dipoles, their manifestation in the sound fields propagating upstream and downstream in the duct is dependent strongly, both quantitatively and qualitatively, on the orientation of these dipole sources relative to the axis of the duct. Both dipole-like and monopole-like ranges exist, and within each range, the relative amplitudes for upstream and downstream propagation vary by over ±40 dB.

Figure 13A:
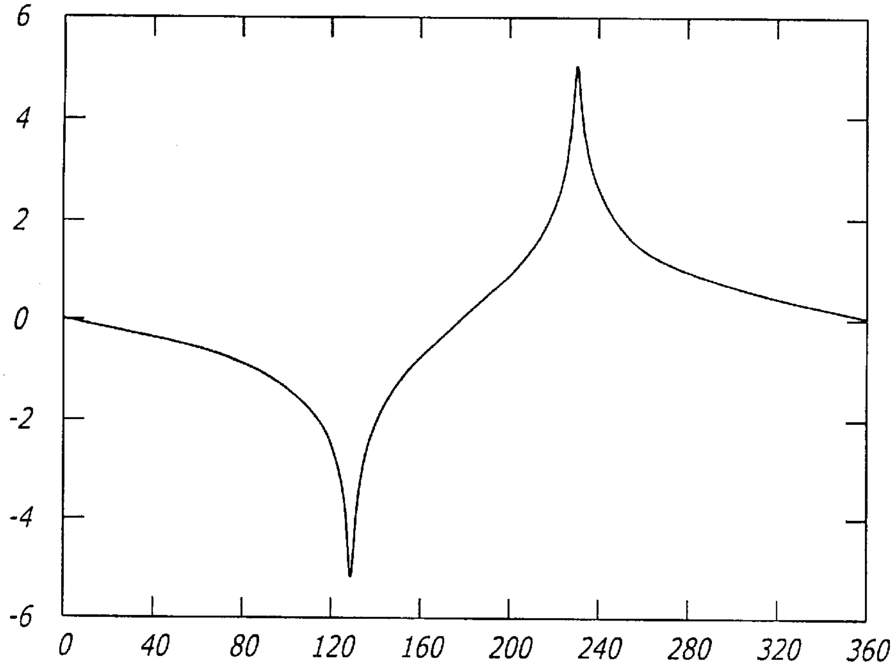
FIGS. 13*a* and 13*b* illustrate curves of the amplitude ratio and phase difference between upstream and downstream radiated sound as a function of the phase difference between signals of amplitude ratio 1.0 to two spaced source arrays.
Figure 13B:
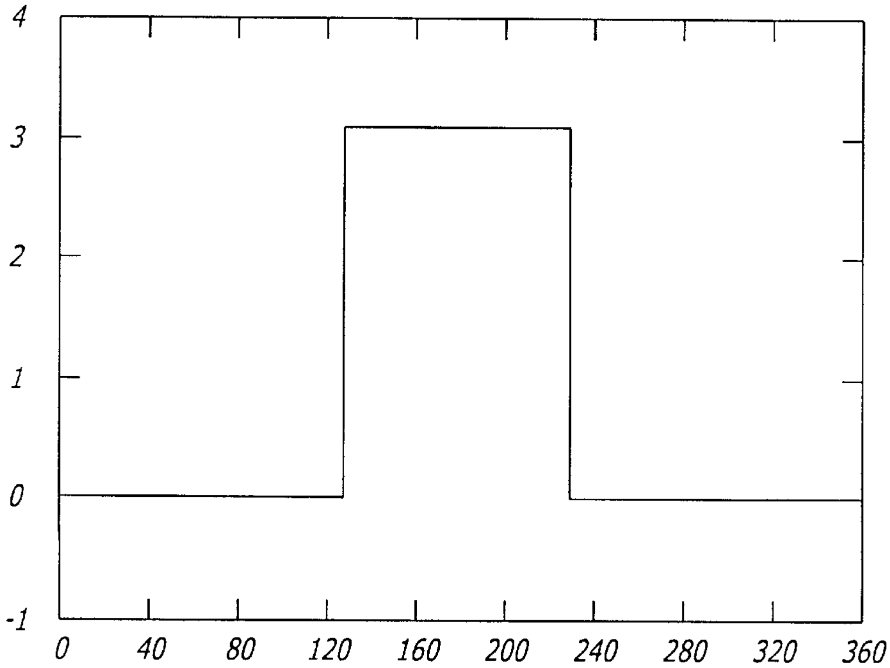

Implementing a dipole cancellation system with an effective axis orientation which matches exactly that of the aerodynamic sources is probably impractical. Further, when multiple modes are considered, it is improbable that the detailed source characteristics are identical for all modes. An alternative approach was investigated and adopted as the final scheme used in the cancellation process. Two equal amplitude monopole arrays were located 25.4 cm apart axially and excited to radiate a (2,0) spinning mode. The relative phase of the signals to the two arrays was varied over 360°. The result of applying this scheme, shown in FIG. 13, exhibits a dipole-like sound source. In the simulation, the full range of inlet/exhaust amplitude ratios and monopole/dipole phase relationships was attained using this simple phase control system.

Adaptive Controller System

A unique and novel system is described to achieve global cancellation of one or more pre-specified modes propagating in a duct. The controller consists of a hybrid combination of analog summing and splitting networks to detect and generate pre-specified modes, and a digital controller which is a single-input, multiple-output adaptive filter whose output drives the analog mode generating circuitry and whose parameters are adapted to minimize the total transmitted power.

The adaptive control system was developed and applied to the active dipole sound source cancellation concept to demonstrate its ability to cancel, in real-time, the cosine component of the (2,0) spinning mode generated in the Axial Fan Facility shown schematically in FIG. 7.

The concept of active sound attenuation has been studied for many years. However the recent development of fast, low cost programmable signal processing hardware has made these systems commercially viable for audio frequency applications. The theoretical basis for active noise control lies in the adaptive signal processing theory developed in the 1960's. Of particular importance is the LMS (least mean square) algorithm developed by Widrow (*Adaptive Signal Processing,* Widrow, B. and Sterns, S. D., Prentice-Hall, Englewood Cliffs N. J., 1985). In 1981, J. C. Burges (*Adaptive Active Sound Control in a Duct: A Computer Simulation,* Burgess, J. C., J. Acoust. Soc. Am., 70, 715–726, 1981) introduced adaptive theory in the context of active noise control and proposed an LMS type algorithm along the lines suggested by Widrow. This work included only computer simulations for cancellation of multiple tones. The key contribution of this work however was the introduction of a model for the auxiliary path. This path has a transfer function that depends on the active sound source, the residual error sensor and propagation path between them. To achieve noise control, this transfer function must be measured or estimated and included in the adaptive algorithm. Accurate modeling of the auxiliary path is a critical factor in achieving good performance. The auxiliary transfer function can be estimated, either on-line or off-line, using standard system identification procedures based on utilizing white noise injection and adaptive filtering.

Adaptive noise control using a FIR (finite impulse response or non-recursive) adaptive filter can be achieved using a modified form of the LMS algorithm, known as filtered-X, in which an estimate of the auxiliary path is included. The non-recursive nature of the FIR filter limits the ability to model feedback in the system. Eriksson noted that the secondary active sound source radiates energy upstream as well as downstream (*Development of the Filtered-U Algorithm for Active Noise Control,* Eriksson, L. J., J. Acoust. Soc. Am., 89, 257–265, 1991). The upstream propagation forms an acoustical feedback plant which contaminates the measurement at the reference microphone. In cases where this feedback is significant, it can be compensated for by using an IIR (infinite impulse response or recursive) adaptive filter in place of the FIR filter. A recursive form of the LMS algorithm for adaptive filtering using IIR filters was first proposed by Feintuch (*An Adaptive Recursive Digital Filter,* Feintuch, P. L., Proc. IEEE, 64 (1), 1622–1624, 1976). This algorithm is commonly referred to as recursive LMS (RLMS). As mentioned above, in active noise control it is necessary to include an auxiliary plant model in the adaptive filter model. In the case of the LMS algorithm for FIR filters, the extension to include the auxiliary path has been termed the "filtered-X algorithm". Similarly, in the case of IIR adaptive filers, the extension of RLMS to include the auxiliary path, has been termed the "filtered-U algorithm." In the application described here, the reference signal is obtained via an optical sensor so that the problem of acoustic feedback does not arise. However, extensions of this approach to broadband applications, in which acoustic transducers are used to measure the reference signal, may benefit from use of the recursive form.

Multi-channel extensions of active noise control principles to the case where there are multiple reference and error transducers and multiple secondary sources have been proposed and studied elsewhere. While it has been noted that these multi-channel systems are capable of canceling higher-order modes, the majority of publications in this area neither constrain the system to produce specified modes nor specifically address performance in terms of individual modal cancellation (*Active Cancellation of Higher Order Modes in a Duct Using Recursively-Coupled Multi-Channel Adaptive Control System,* Roberstein, S. P., Popovich, S. R., Melton, D. E., Allie, M. C., Proc. Inter-Noise 92, 337–340, Toronto, Canada, Jul. 1992). The current study deals with the problem of cancellation of one or more specific modes. Tichy (*Active Systems for Sound Attenuation in Ducts,* Tichy J., Proc. IEEE-ICASSP88, 2602–2605, 1988) presents an analysis of active modal cancellation. His controller is based on estimated coefficients of a modal expansion of the pressure field. Results are presented only for plane-wave propagation. Since the method does not take into account the transfer functions between the reference and error microphones or the transfer function of the secondary sources, this method is not expected to perform well. Baumann and Greine (*Number of Error Microphones for Multi-Modal Cancellation,* Baumann, D. C., Greiner, R. A., Proc. Inter-Noise 92, 345–348, Toronto, Canada) extend this approach to multiple modes by setting up a system of linear equations whose solution is used to control the secondary source. Performance is again expected to be poor for the same reasons. Goodman and Burlage (*Active Noise Cancellation in Ducts in the Presence of Higher Order Modes,* Goodman, S. D., Burlage, K. G., 441–448) describe a multiple input multiple output (MIMO) controller for modal cancellation in a duct. They note that for cancellation of N modes, a minimum of N input sensors and N actuators are required. It will become clear in the following, that for the circular duct application considered here, this number is insufficient for practical control of higher modes. Goodman and Burlage describe how, through driving the actuators and combining error signals with appropriate phasing, one can avoid generating and detecting specific modes. However the reverse, i.e. combining sensors to detect and generate specific higher-order modes is unique to the current application. Using prior information regarding the dominant modes which can be generated in the system, the complexity of the controller can be greatly reduced by constraining the system to produce only the dominant mode or modes. Furthermore, since the system is constrained to produce only pre-specified modes, performance of this system will be superior to general MIMO controllers in which other unwanted modes will be produced as a by-product of the multi-channel control procedure. Another unique feature of the system described here is the ability to provide global cancellation through the use of pairs of arrays of microphones upstream and downstream of the secondary sources configured to separate transmitted and reflected components of the signal.

Controller Hardware

Figure 14:
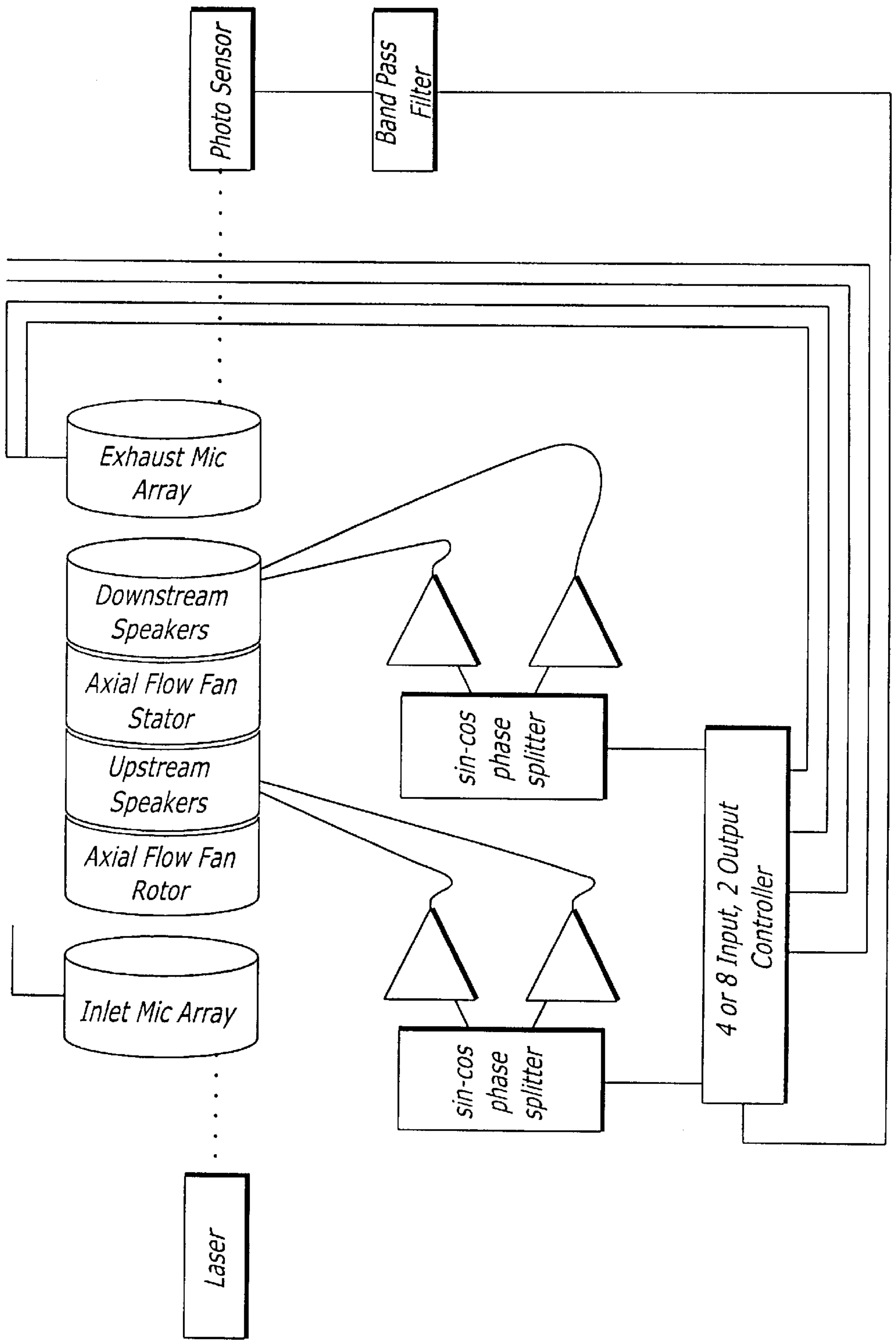
FIG. 14 is a schematic of the spinning mode active control system used of the present invention used to globally cancel the (2,0) mode with two axially separated monopole loudspeaker arrays mounted across the stator vanes of an axial flow fan.

FIG. 14 is a schematic of the spinning mode active control system used to globally cancel the (2,0) mode with two axially separated monopole loudspeaker arrays, mounted across the stator vanes in the axial flow fan. The hardware consists of the following principal components:

1. A laser/photo sensor signal is used to measure the rotor blade passing frequency and derive a BPF reference signal. It is the main input to the control system. Its amplitude and delay are adjusted by the control algorithm and DSP board. Two controlled outputs are available from the DSP board, each with individual control.
2. The eight Mode 2 sin/cosine microphone array signals are used by the controller to assess total radiated acoustic power.
3. The two output signals from the controller are split into quadrature components by a Hilbert Transform processor and sent, via individual power amplifiers, to the sine and cosine loudspeaker arrays located upstream and downstream of the fan stator vanes.

A dual array of source transducers, spaced within λ/2, which straddle the aerodynamic source region in the fan, duplicates the sound field radiated by a dipole or monopole of arbitrary orientation when driven by signals of appropriate amplitude and phase relationship. Although technically the number of sources for control of a spinning mode order (m,n) is (n+1)(2m+1) as with the microphone arrays, to make the most efficient use of transducer output, i.e. to maximize coupling to the propagation mode to be controlled, transducers are located at modal antinodes. For control of the (2,0) mode, arrays of eight sources are used, four for the cosine orientation component and four for the sine orientation component. This has the further advantage of allowing transducers to be driven from a single power amplifier per sub-array, if only one mode is to be controlled.

For simultaneous control of multiple propagation modes, transducers are driven by individual power amplifiers activated by signals from a mode-combining matrix which is a converse of the microphone mode separation matrices.

Figure 15:
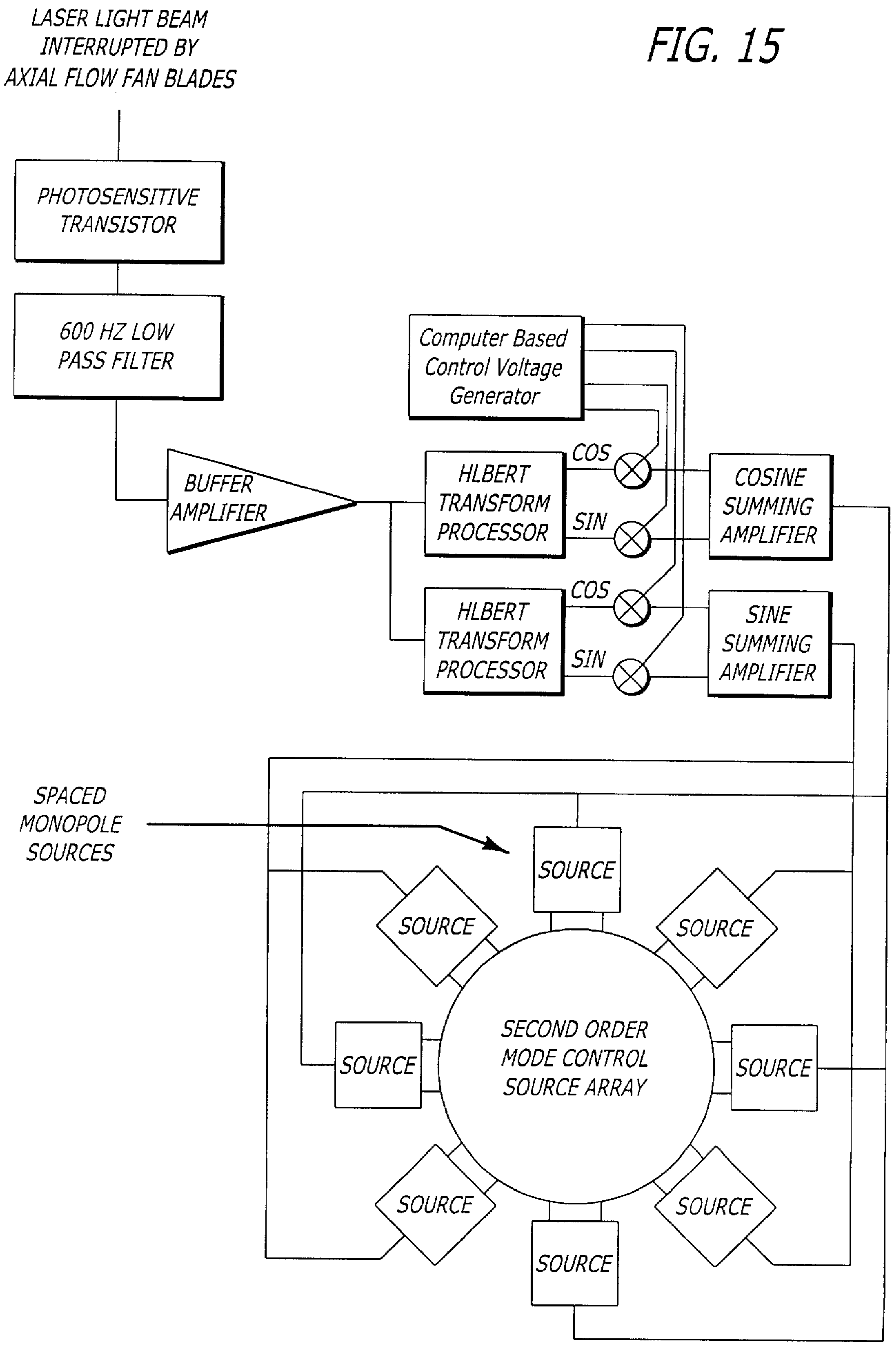
FIG. 15 is a schematic diagram of an axial flow fan second order spinning mode active cancellation development system.

FIG. 15 is a schematic diagram of a single-reference multi-output multi-error (SIMOME) adaptive active noise control system for providing cancellation of a single mode in a cylindrical duct. The system uses a single reference transducer to generate a sinusoidal signal of frequency equal to the rotor blade passage rate. A digital controller is used to adaptively modify the amplitude and phase of this signal which is then used to drive an acoustic dipole array. FIG. 15 also displays a schematic of a single-reference multi-output multi-error (SIMOME) adaptive active noise control system for providing absorption of a single mode in a cylindrical duct. The system uses a single reference transducer to generate a sinusoidal signal of frequency equal to the blade passage rate. A digital controller is used to adaptively modify the amplitude and phase of this signal which is then used to drive an acoustic monopole array. The adaptive scheme is designed to minimize the total power propagating in the selected mode as measured by the microphone arrays and analog summing networks described above. Depending on the positioning of the elements of the dipole array and the microphone arrays, a single adaptive scheme can be used to achieve global absorption of the sound fields in both the inlet and exhaust duct sections. The results described in this report are for cancellation of the cosine component of the (2,0) mode in the test duct inlet and exhaust sections. However, the scheme is general for any non-radial mode. Furthermore the approach extends readily to absorption of single radial modes and multiple modes.

The single reference input uses an optical sensor to produce a periodic signal with fundamental frequency equal to the rotor blade passage frequency. The light beam from a small laser was directed through the fan towards a light-sensitive transistor. The periodic interruption of the light beam by the passing fan blades produced a quasi-rectangular wave which was low-pass filtered to form a sinusoidal signal for the control system.

Active cancellation is achieved by driving an array of eight acoustic "dipoles," each consisting of a pair of JBL 2426J electrodynamic drivers spaced approximately 10 inches apart and arranged parallel to the central axis of the duct. The "dipoles" are equally spaced in angle by 45°. These sound sources can be equivalently viewed as two arrays of eight monopoles. Each array is configured in two sets of four elements with a spacing of 90° between each driver in each set as illustrated in FIG. 15. In a single group, the elements are driven with 180° phase advance relative to their neighbors, thus generating a stationary (2,0) mode for frequencies above the cut-on frequency of approximately 550 Hz (for STP atmospheric conditions). By independently driving the two groups of drivers, which are rotated by 45° from each other around the circumference of the duct, arbitrary spinning (2,0) modes were generated by superposition of the two standing modes. The simultaneous control over the upstream and downstream components generated by the dipole array is achieved by independently driving the two groups of elements in each of the two monopole arrays. Thus, a total of four signals are required for full control of the (2,0) spinning modes generated by the acoustic dipole array.

The four control signals which drive the acoustic array are generated by filtering the sinusoidal BPF reference signal. Filtering is performed by sampling the BPF reference signal through an analog-to-digital converter (ADC), passing this signal through a multi-channel adaptive digital filter, and sending the output to a four channel digital to analog converter (DAC). The specific form of the adaptive filter is given below. To summarize, a single-reference multi-output multi-error (SIMOME) variation of the well known filtered-X algorithm is used to adaptively select the impulse response of the four FIR filters through which the sampled BPF reference signal is passed to generate the four control signals required to drive the resonator array. The adaptive filters are designed to minimize the total power in the (2,0) mode transmitted upstream and downstream of the dipole array. The sum squared of the two quadrature components generated by the summing networks described earlier provide instantaneous estimates of the power propagating in the (2,0) mode. Thus a total of four signals (the transmitted upstream and downstream quadrature components) must be monitored to guide the adaptive filter.

The novelty of this control scheme is that by utilizing knowledge of the mode transmitted in the duct, the complexity of the control algorithm is reduced dramatically. Furthermore, since the system is configured to only generate the desired mode, one can expect superior performance since unwanted plane-waves and other modes will not be generated. In contrast, a generic multi-channel active noise controller would require that each of the eight drivers installed in the two resonator array cavities be independently driven and that a total of eight input channels (i.e., the transmitted component for each element of the upstream microphone arrays) be monitored. As will become clear below, computational complexity is roughly on the order MN where M is the number of input channels and N the number of output channels. Thus the relative complexity of our system is 4×4.

The digital controller used in this research project was implemented using a Spectrum TMS320C30 System Board which is a development system for real-time signal processing built around the TMS320C30 32-bit floating point, 60 ns digital signal processing chip. Analog interfaces are provided by two 16-bit Burr-Brown PCM78 ADCs and two 16-bit Burr-Brown PCM56 DACs. The board is equipped with resistor programmable fourth-order Butterworth anti-aliasing and reconstruction filters which were programmed for a 3 dB cut-off of 1 KHz. The number of I/O channels was supplemented by a Spectrum 4-channel analog I/O board equipped with four 16-bit analog input channels (ADCs) and two 16-bit output channels (DACs) equipped with third-order Butterworth anti-aliasing and reconstruction filters, again programmed for a 3 dB cut-off of 1.2 KHz. This arrangement provides the required number of I/O channels: four input channels for the transmitted quadrature components of the upstream and downstream (2,0) mode, one input channel for the BPF reference signal, and four output channels for control of the acoustic array. Software was written using the standard Texas Instruments TMS320C30 assembler and compiler.

Control Algorithm

Figure 16:
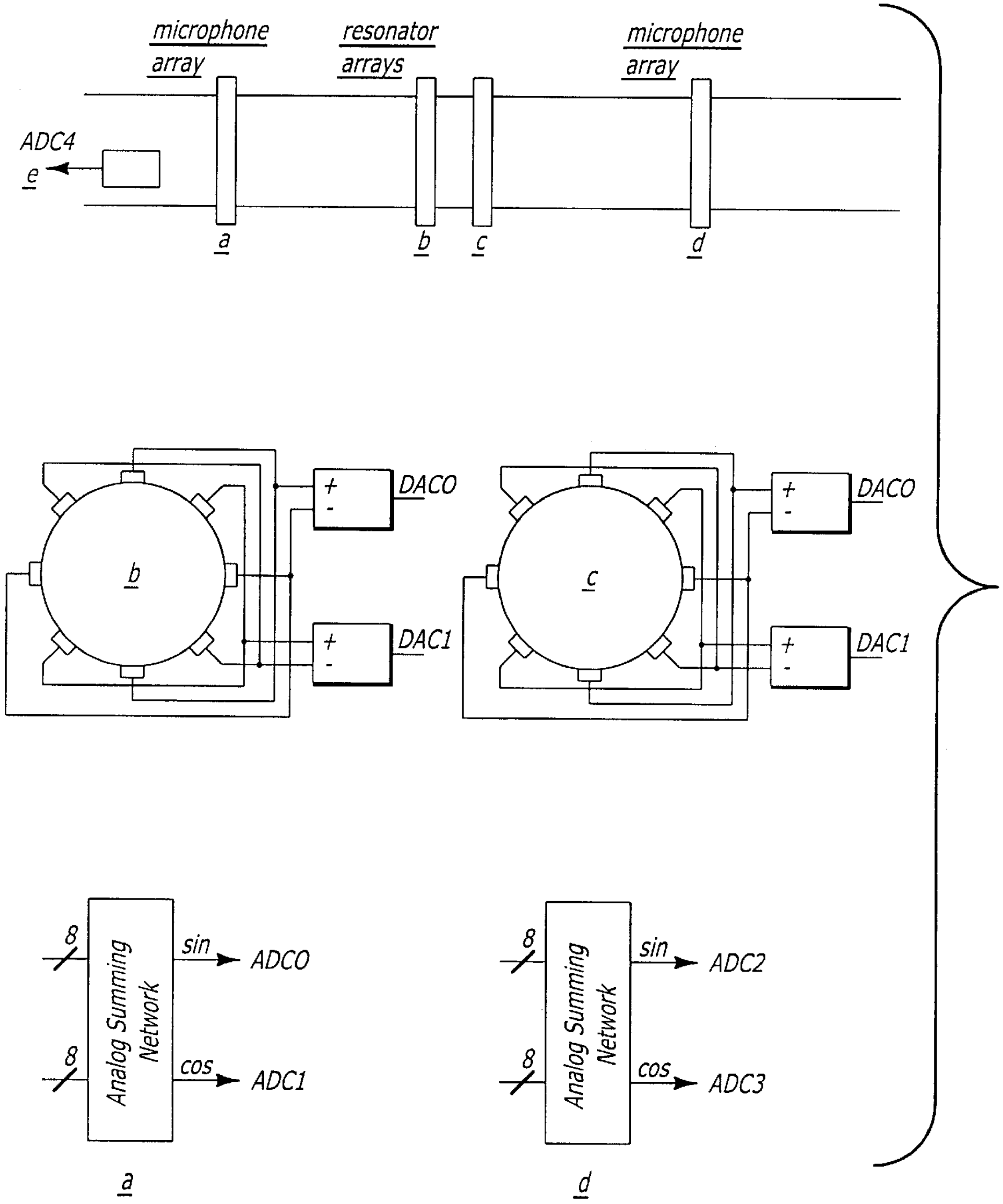
FIG. 16 illustrates the arrangement of the controller of FIG. 15.
Figure 17A:
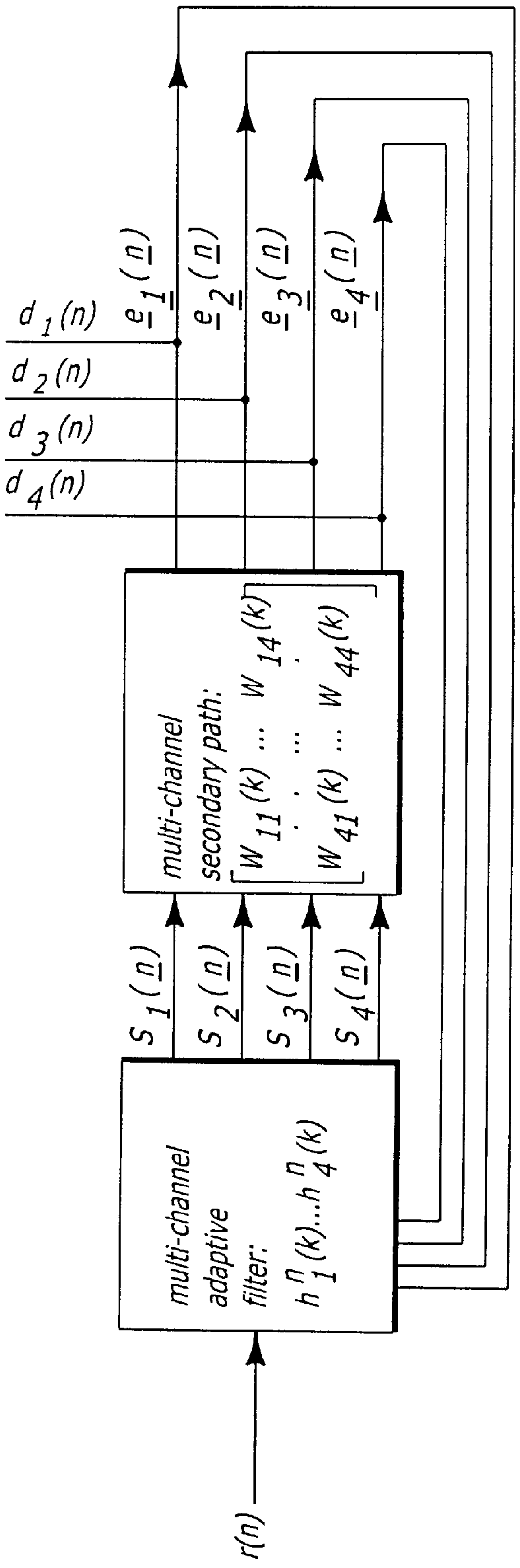
FIG. 17*a* illustrates an equivalent model for which the duct, analog networks, microphone and resonator arrays and the analog electronics are all represented by an equivalent four input/four output system.

The controller was developed as a multi-channel variation of the well known filtered-X noise cancellation scheme. FIG. 16 shows the arrangement of the controller of FIG. 15 in terms of the required inputs and outputs for the adaptive controller and how they interface to the other electronic components and transducers. FIG. 17*a* shows an equivalent model for the system in which the duct, analog networks, microphone and resonator arrays and the analog electronics are all represented by an equivalent four input/four output system. The inputs to this equivalent system are the signals produced by filtering the BPF reference with each of the four digital, FIR, adaptive filters. The outputs of the system are the digitized samples from the upstream and downstream quadrature components of the (2,0) mode as measured using the microphone arrays and analog summing networks. For PBF frequencies beyond the (2,0) cut-on frequency, this system is well approximated as a being both linear and time invariant. Using this equivalent model for the system, the adaptive filter equations were developed.

Let:

$e_i(n)$=error signal at $i^{th}$ input channel, I=1 . . . M r(n)=BPF reference signal $h^n_j(k)$=FIR impulse response of adaptive filter at $j^{th}$ output channel, k=0, . . . K−1, j=1 . . . J $W_{ij}(k)$=Impulse response between $j^{th}$ output channel and $i^{th}$ input channel $d_i(n)$=Contribution to $e_i(n)$ from fan-generated modes The error signals are the quadrature components of the (2,0) mode as measured at the upstream and downstream microphone arrays. These signals are generated by a superposition of the (2,0) mode generated by the fan and the four standing (2,0) modes generated by the two groups of drivers in each of the speaker arrays. Thus $$e_i(n) = d_i(n) + \sum_{j=1}^{J} W_{ij}(k) * h_j^n(k) * r(n) \tag{10}$$

where * denotes a discrete time convolution sum. Note that the transfer function of the multi-channel system, $W_{ij}(k)$ i=1, . . . 4, j =1, . . . 4, is unknown and must also be determined using the adaptive filter described below.

Global cancellation of the (2,0) mode can be achieved by minimizing the total power as measured in the error signal channels. The instantaneous power, in terms of the equivalent model, is given by $$E(n) = \sum_{i=1}^{M} e_i(n)^2 = \sum_{i=1}^{J}\left[d_i(n) + \sum_{i=1}^{J}\sum_{k=0}^{K-1} y_{ij}(n-k)h_j^n(k)\right]^2 \tag{11}$$

where $$y_{ij}(n) = \sum_k r(n-k)W_{ij}(k) \tag{12}$$

The sequences $y_{ij}(n)$ are the result of convolving the BPF reference with the transfer functions $W_{ij}(k)$ between each of the inputs and each of the outputs in the equivalent system illustrated in FIG. 17. The coefficients of the adaptive filters are updated as each new sample arrives using an LMS (Least Mean Squares) procedure. The LMS procedure can be viewed as a steepest descent algorithm in which the mean square error (or signal power) is approximated by the instantaneous squared error E(n). For this model, the instantaneous gradient is $$\frac{\partial E(n)}{\partial h_j^n(k)} = 2\sum_{i=1}^{M} e_i(n)y_{ij}(n-k) \tag{13}$$

Thus the multi-channel adaptive algorithm requires updating of each of the adaptive FIR filters according to the procedure $$h_j^{n-1}(k) = h_j^n(k) + 2\gamma^n \sum_{i=1}^{M_i} e_i(n)y_{ij}(n-k); \tag{14}$$

$$k = 0, \ldots K-1;\ j = 1, \ldots J$$

where $\gamma^n$ is a positive scalar step size which must be selected. In practice the transfer functions $W_{ij}(k)$ are approximated using the results of the adaptive system identification scheme described below. Once the filter coefficients have been updated using Eq. (14), the new output vector is computed by convolving the updated filter coefficients with the BPF reference to yield, $$s_j(n) = \sum_k r(n-k)h_j^n(k) \tag{15}$$

Identification of the Secondary Transfer Functions

Figure 17B:
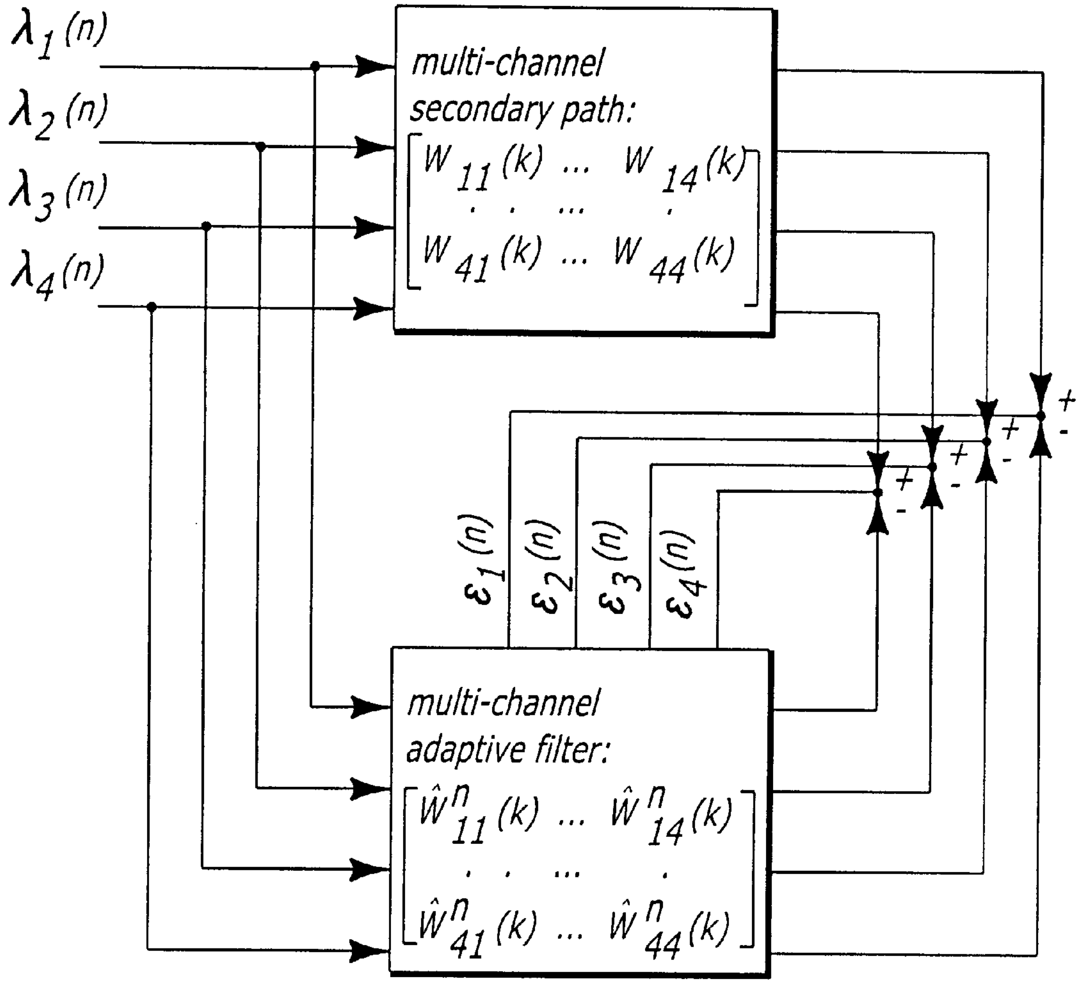
FIG. 17*b* illustrates an arrangement for identification of the secondary transfer function using standard white noise injection techniques in which a conventional LMS multichannel adaptive filter in which independent identically distributed (IID) white noise is injected into each of the output channels and simultaneously into an adaptive filter.

To implement the adaptive scheme defined by Eq. (14), the filtered signals $Y_{ij}(n)$ must be computed. This in turn requires knowledge of the transfer functions $W_{ij}(k)$. The $W_{ij}(k)$'s determine the effective amplitude and phase change in a scalar sinusoidal signal between the $i^{th}$ output channel and the $j^{th}$ input or error. Between the input and output channels, the sinusoidal signal excites a stationary (2,0) mode through one of the four groups of four speakers—in turn this (2,0) mode excites the arrays of microphones, which through the analog summing networks produce the four scalar upstream and downstream quadrature components (the error inputs). Since the system must work for a range of frequencies above the (2,0) cut-on frequency, the transfer function must be determined over a broadband range up to the maximum frequency of interest. This system identification can be realized using standard white noise injection techniques. One arrangement for identification of the secondary transfer function is illustrated in FIG. 17*b*. This procedure uses a conventional LMS multi-channel adaptive filter in which independent identically distributed (IID) white noise is injected into each of the output channels and simultaneously into an adaptive filter. The coefficients of the filter are adapted to minimize the mean squared difference between the output of the adaptive filter and the signals recorded at the output of the analog summing networks.

Let:

$\epsilon_i(n)$=error signal at $i^{th}$ input channel, i=1 . . . M $\lambda_j(n)$=white noise output through $j^{th}$ channel, j=1, . . . J $W_{ij}(k)$=Impulse response between $j^{th}$ output channel and $i^{th}$ input channel $\hat{W}_{ij}(k)$=Impulse response of the adaptive filter which models $W_{ij}(k)$ The error signal whose power is to be minimized is the difference between the result of passing the white noise through the real system $W_{ij}(k)$, and through the adaptive filter $W_{ij}^{n}(k)$ is $$e_i(n) = \sum_{j=1}^{J}\sum_k \hat{W}_{ij}^n(k)\lambda_j(n-k) - \sum_{j=1}^{J}\sum_k W_{ij}^n(k)\lambda_j(n-k) \tag{16}$$

The instantaneous estimate of the error signal power is $$\Gamma(n) = \sum_i^{I} \varepsilon_i(n)^2 \tag{17}$$

with corresponding gradient $$\frac{\partial \Gamma(n)}{\partial \hat{W}_{ij}(k)} = 2\varepsilon_i(n)\lambda_j(n-k) \tag{18}$$

Thus the LMS algorithm which provides estimates of the secondary transfer function has the following form, $$\hat{W}_{ij}^{n-1}(k)=\hat{W}_{ij}^{n}(k)+2\gamma^n\epsilon_i(n)\lambda_j(n-k) \tag{19}$$

The advantage of performing system identification using white noise injection is that the system can be continuously monitored on-line by adding white noise to the filtered BPF signal using and simultaneously updating the secondary transfer functions using Eq. (19) and the primary adaptive filters using Eq. (14).

Practical Considerations

Figure 18:
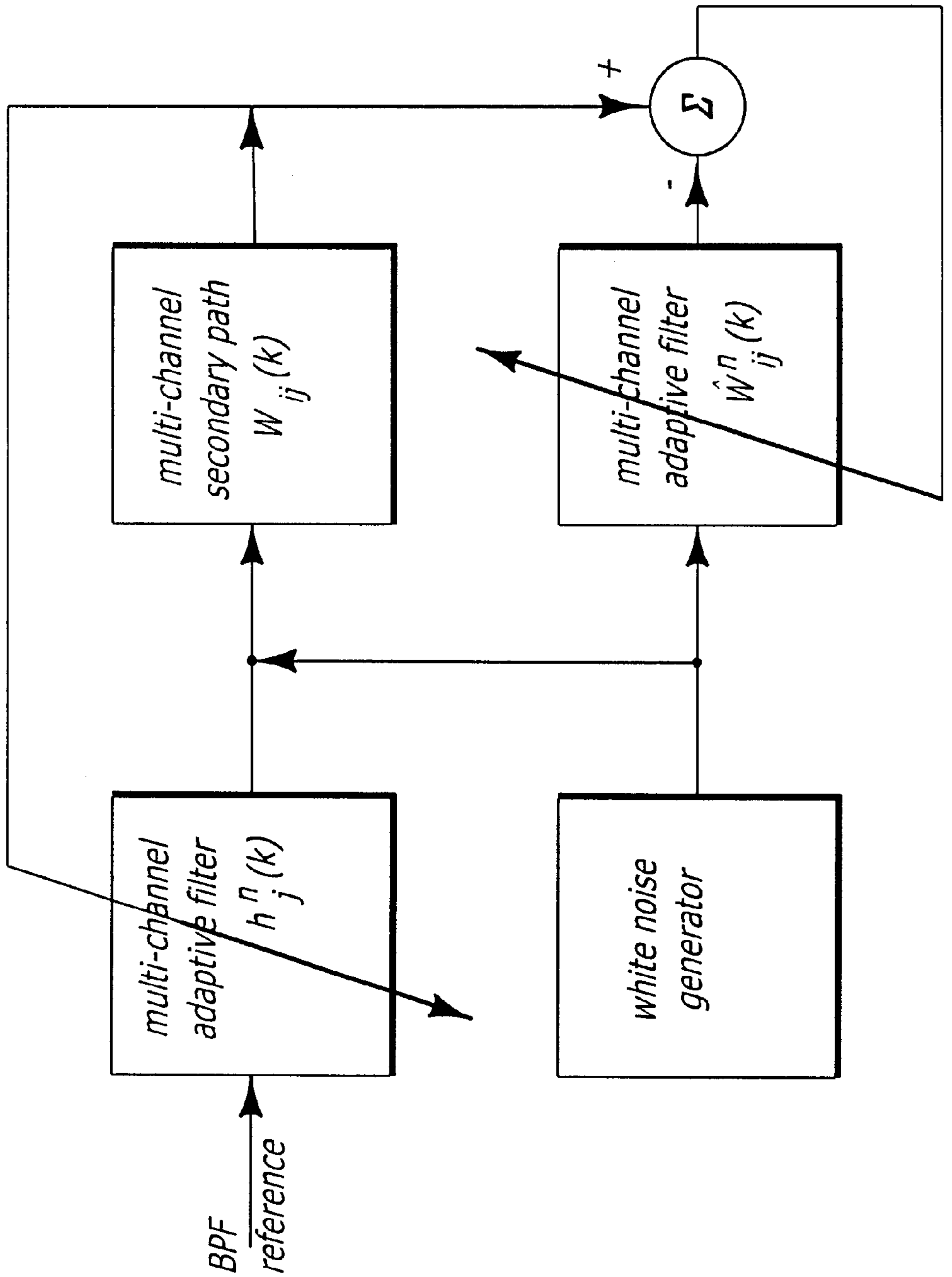
FIG. 18 is a schematic of the adaptive algorithm defined by Eq. (14) as implemented on a Spectrum TMS320C30 System Board.

The algorithm described above was implemented on the Spectrum TMS320C30 System Board and other hardware described above. A schematic for the overall algorithm is shown in FIG. 18. The software consists of two stages:

1. An initialization stage wherein the secondary transfer functions are identified using the white noise injection scheme described above with the primary control-off.
2. Once the initialization is completed, control is initiated using the controller described above. Optional continuous updating of the secondary transfer function can be performed through continued noise injection. For short experimental runs on the order of several minutes, this is unnecessary.

The parameters under which the adaptive algorithm was run are summarized in Table IV below.

C. TEST RESULTS

Figure 19A:
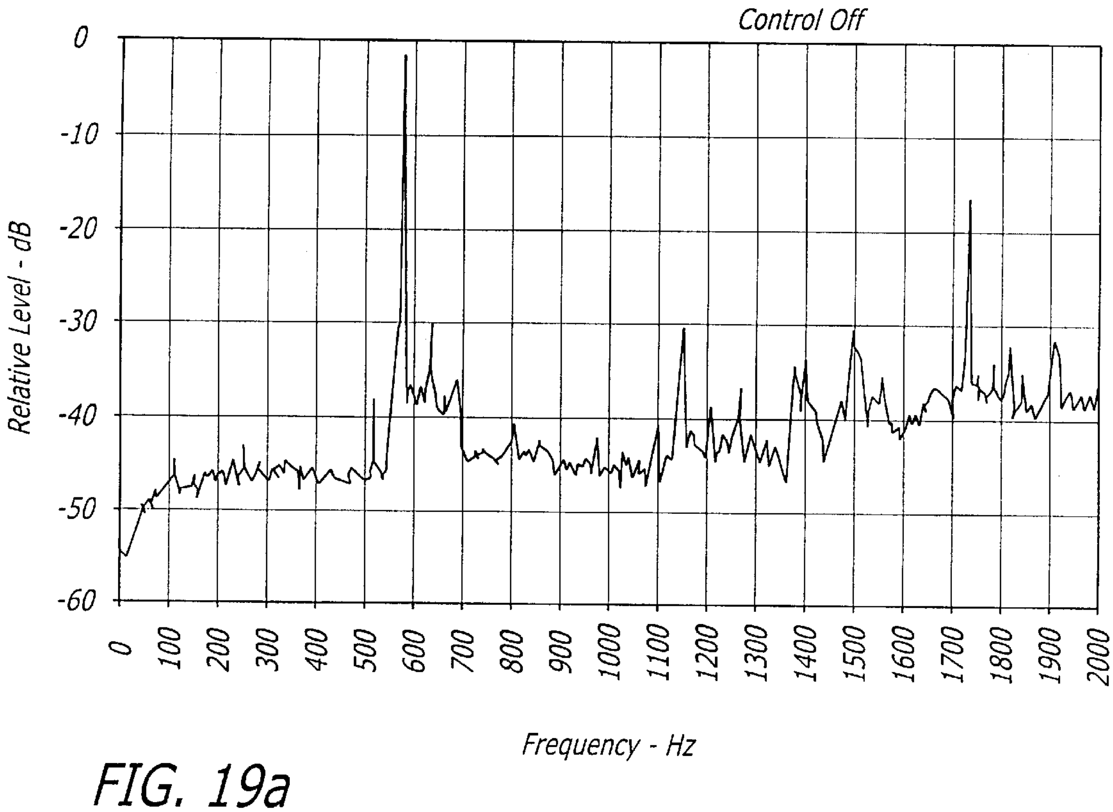
FIG. 19 illustrates that the source cancellation system of the present invention attenuated the rotor-stator generated (2,0) cosine component propagating in the duct inlet (upstream) by approximately 29 db.
Figure 19B:
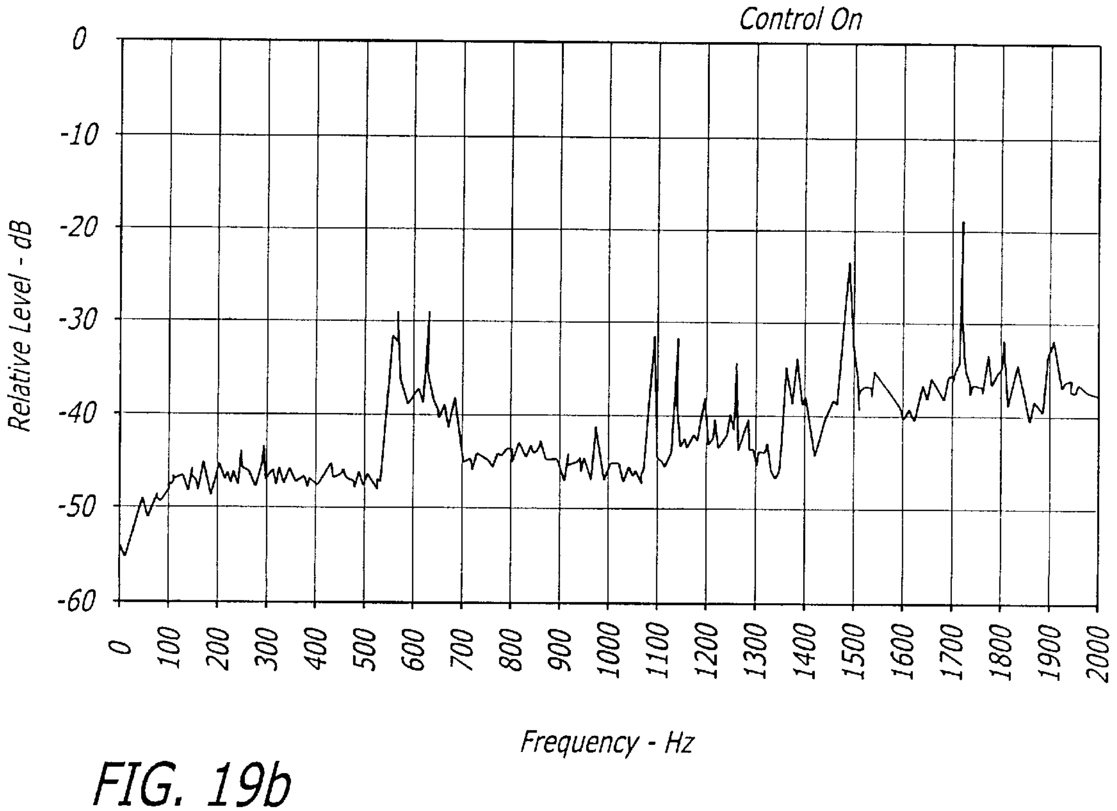
Figure 20A:
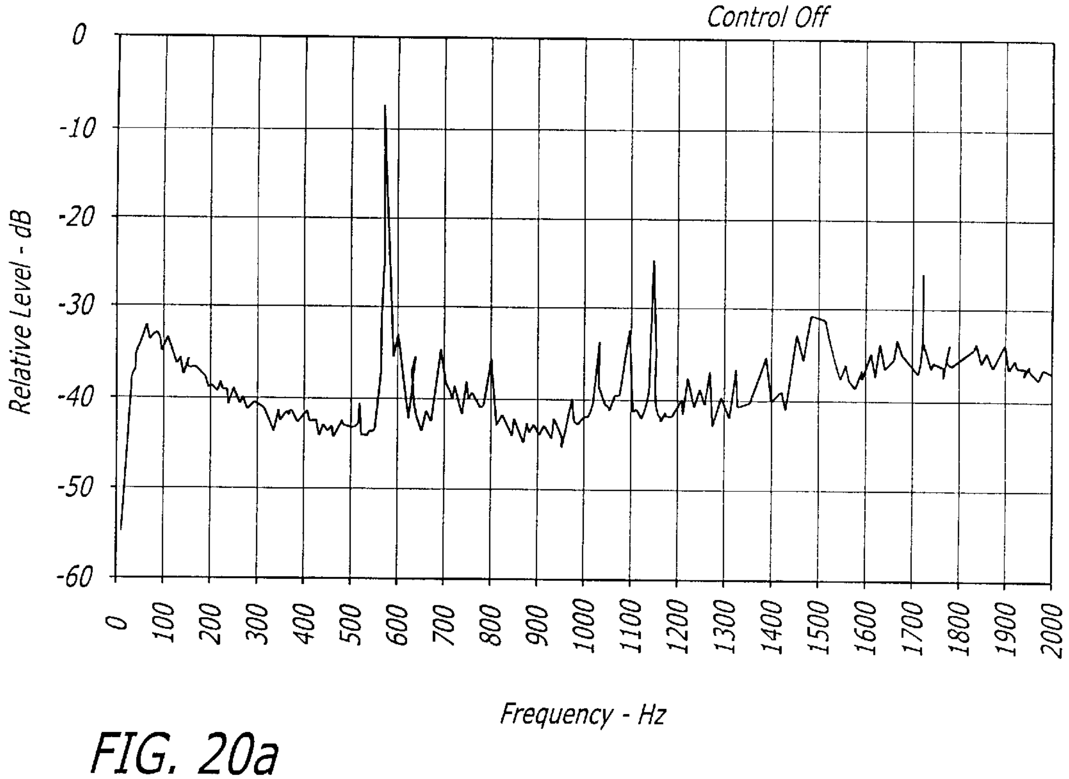
FIG. 20 illustrates that in the active control Helmholtz resonator experimental program test of the present invention, the (2,0) cosine component propagating in the duct exhaust (downstream) was attenuated by approximately 19 db.
Figure 20B:
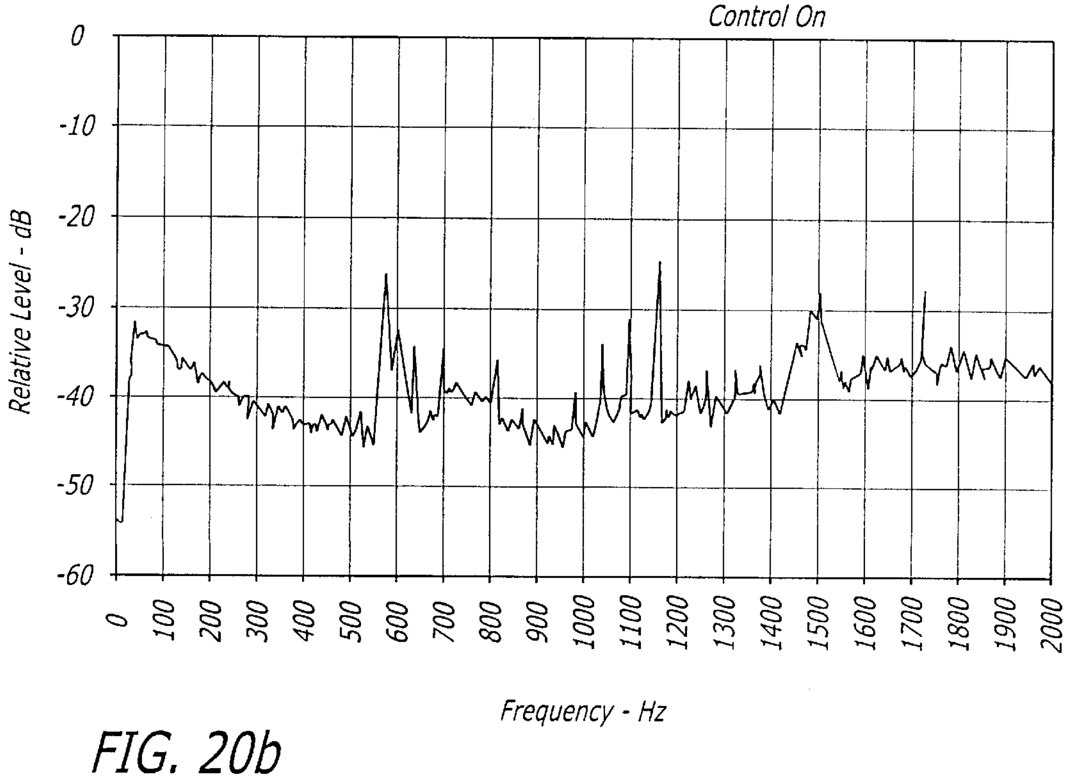

FIGS. 19 and 20 summarize the noise reductions achieved by installing the adaptive controlled source cancellation system into the axial fan test facility shown schematically in FIG. 7. FIG. 19 shows that the source cancellation system attenuated the rotor-stator generated (2,0) cosine component propagating in the duct inlet (upstream) by approximately 29 db. FIG. 20 shows that the corresponding (2,0) cosine component propagating in the duct exhaust (downstream) was attenuated by approximately 19 db. The differences between the inlet and exhaust cancellations are believed to be associated with aft-duct motor housing generated standing wave complications and the fact that the sound field, without control, in the exhaust duct is significantly weaker than that in the inlet duct.

TABLE IV

Summary of Adaptive Algorithm Parameters

| | |
|---|---|
| Sample Rate | 3,000 Hz |
| Cut-off frequency of anti-aliasing and reconstruction lowpass filters | 1,000 Hz |
| Length of primary adaptive filters | 64 taps (×4 filters) |
| Length of secondary adaptive filters | 128 taps (×16 filters) |

2. ACTIVE RESONATOR INVENTION

An experimental program was undertaken to demonstrate the active control Helmholtz resonator invention. The demonstration consisted of absorbing inlet propagating (1,0) and (2,0) BPF modes generated in the axial fan test facility shown schematically in FIG. 21 in both reflected and transmitted directions. Detailed descriptions of the test facility and data acquisition and reduction schemes and sound absorption performance achieved using the active resonator invention are presented in Sections A and B below.

A. TEST FACILITY AND DATA REDUCTION SCHEME

The same axial fan test facility and data acquisition and control hardware/software used to validate the source cancellation concept was also used to validate the active control sound absorption concept. Starting on the right side of FIG. 21, the system components consist of (1) a laser, located upstream of the duct inlet, emitting a beam that passes through the fan and incident on an optical sensor located downstream of the duct exhaust, used to measure rotor speed and to derive a blade passage signal, (2) a wire mesh screen and honeycomb flow straightener attached to a Bell Mouth inlet to stabilize flow disturbances generated principally from inlet ground vortices, (3) two arrays of eight microphones per array arranged in eight pairs of two microphones with each pair spaced circumferentially 45° apart to measure separately the inlet and exhaust propagating sound pressure fields in the space between the duct inlet and the fan, (4) two arrays of eight active control Helmholtz resonators per array located upstream of the rotor-stator vanes, (5) an array of nine one-quarter inch thick rods located upstream of the axial fan rotors to generate (1, 0) modes at BPF, (6) a Joy Axial Fan containing 10 rotors and eight stationary guide vanes and (7) two arrays of eight microphones per array arranged in eight pairs of two microphones with each pair spaced 45° apart to measure separately the inlet and exhaust propagating sound pressure fields in the space between the fan and the duct exhaust. A variable speed controller (not shown) was used to vary the fan speed over the range 0–3530 RPM.

Applying Eq. (1) to the axial fan shown schematically in FIG. 21, which consists of ten rotor blades, eight stator vanes and nine spoiler rods, the (2,0) mode is generated at the blade passing rate (n=1) by rotor/stator interaction for p=−1 and the (−1,0) mode is generated at the blade passing rate by spoiler/rotor interaction for p=−1. For the 24-inch diameter fan duct, the cut-on frequency of the (2,0) and (1,0) spinning modes at normal room temperatures are about 550 and 330 Hz, respectively. With the spoiler rods extended, the (−1,0) mode at BPF is an issue above 2000 RPM and the (2,0) mode at 2×BPF is an issue above about 1760 RPM.

In-Duct Cancellation

Figure 21:
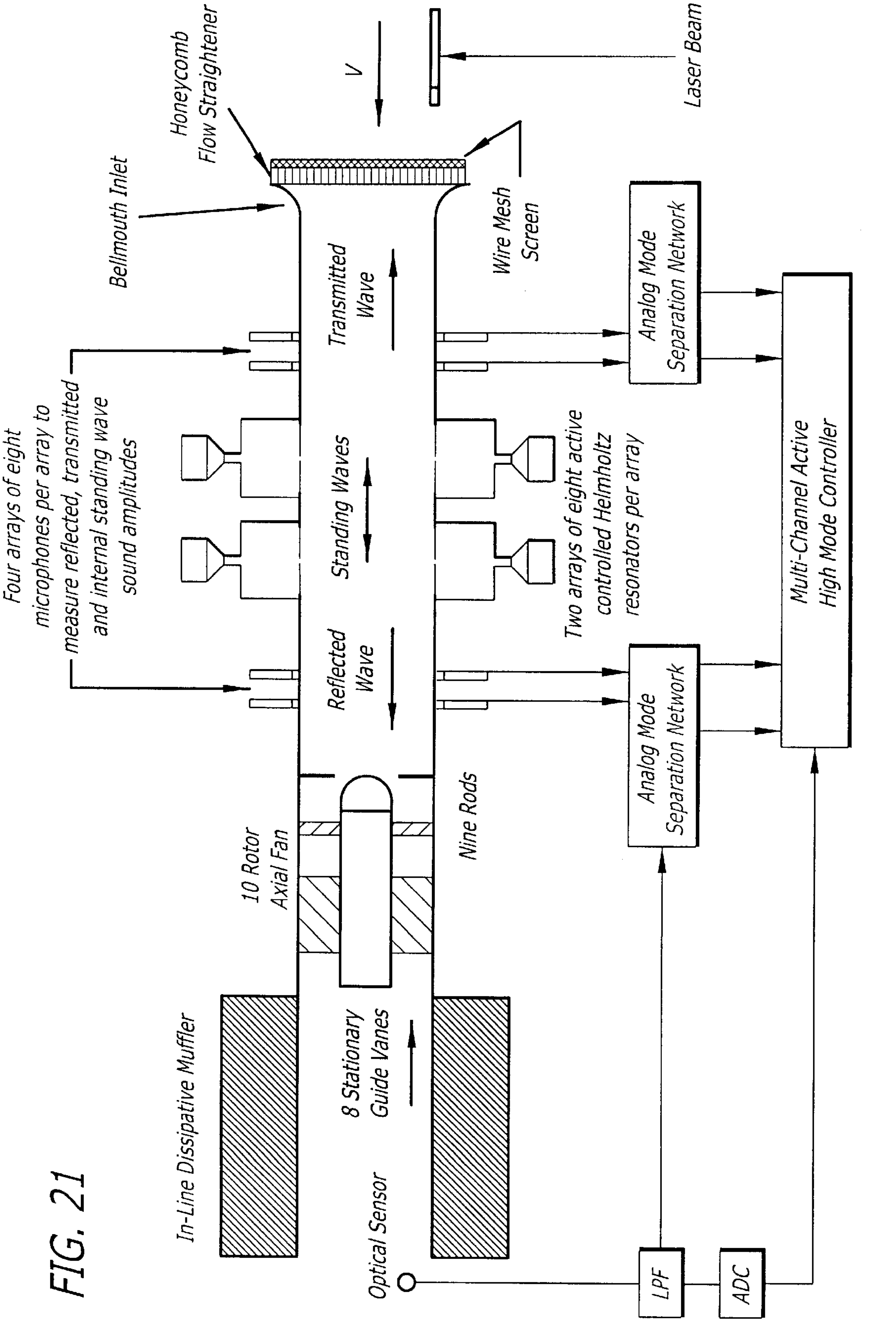
FIG. 21 is a schematic of an axial fan test facility for an experimental program to demonstrate the active control Helmholtz resonator invention for absorbing inlet propagating (1,0) and (2,0) BPF modes generated in the axial fan in both reflected and transmitted directions.
Figure 22A:
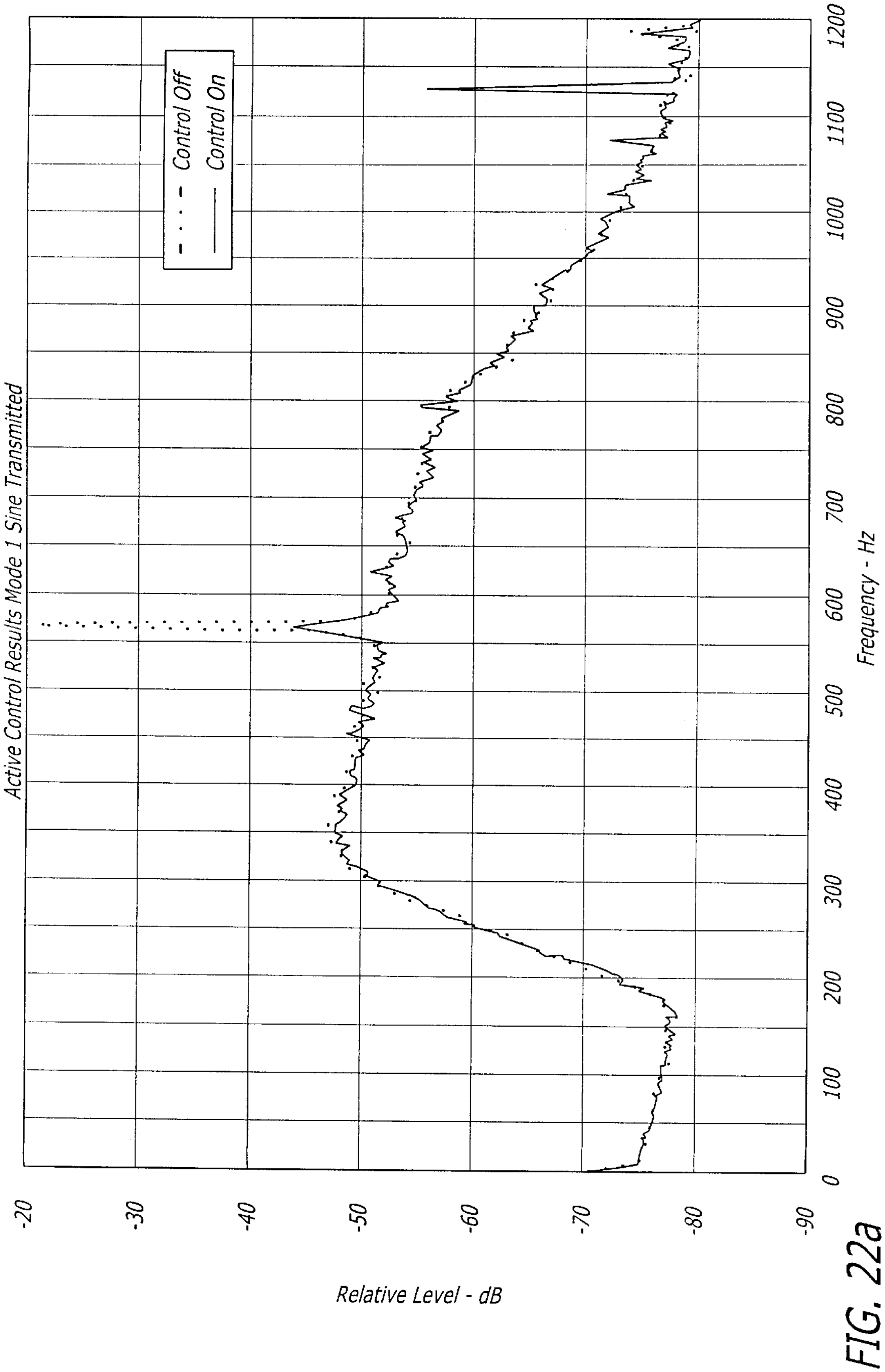
FIGS. 22(*a–d*) for the (1,0) mode.
Figure 22B:
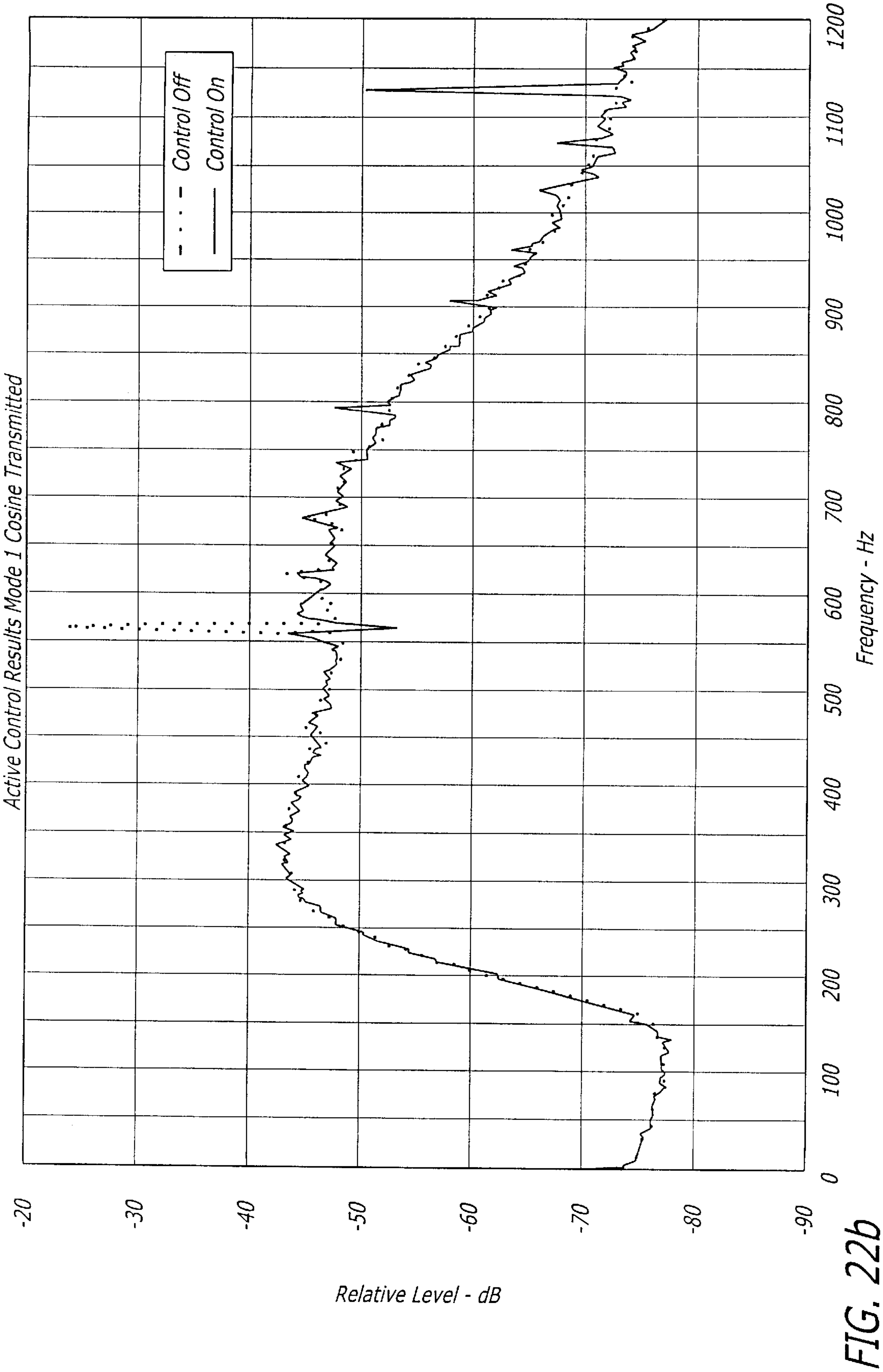
Figure 22C:
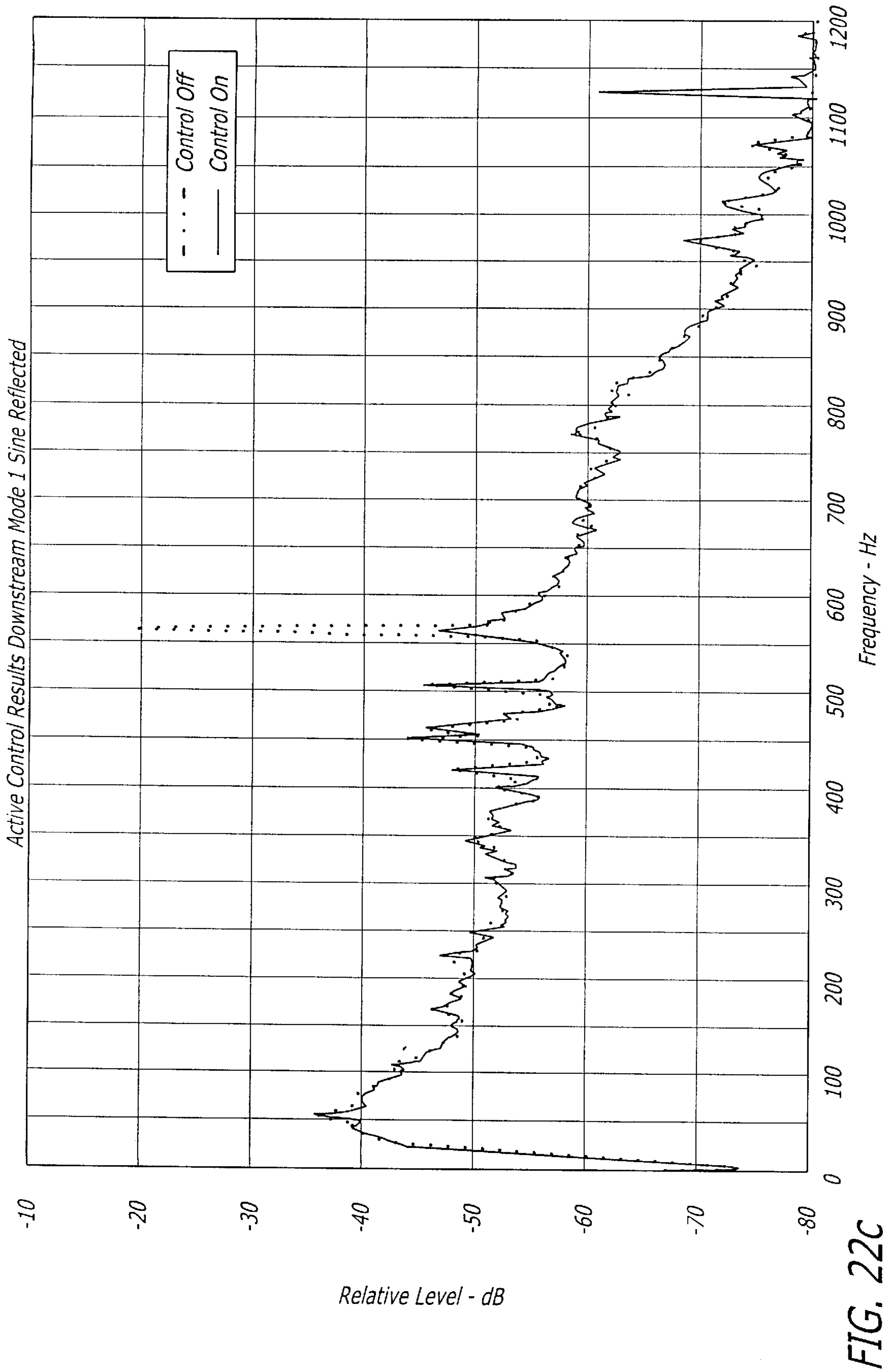
Figure 22D:
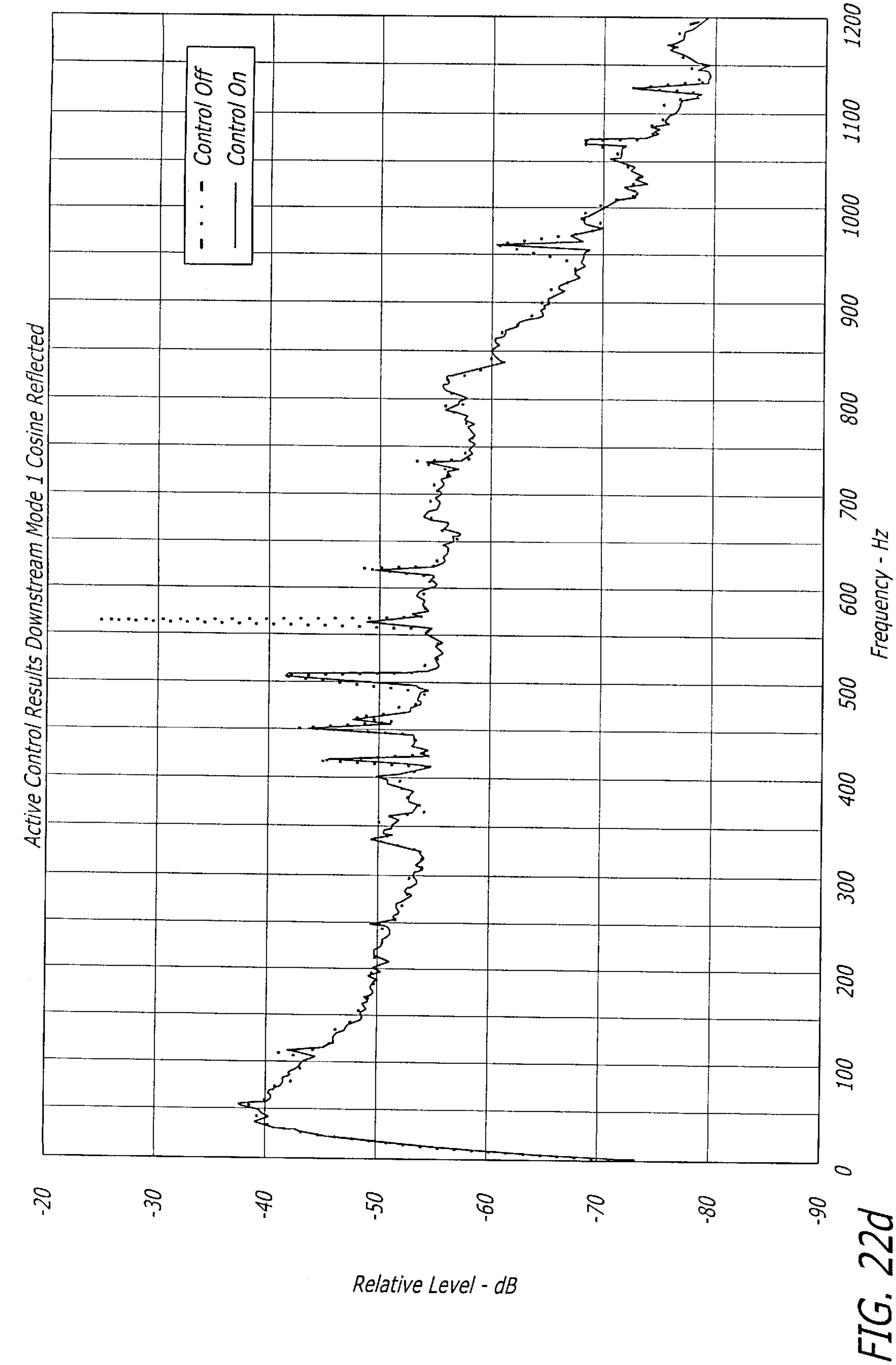
Figure 23A:
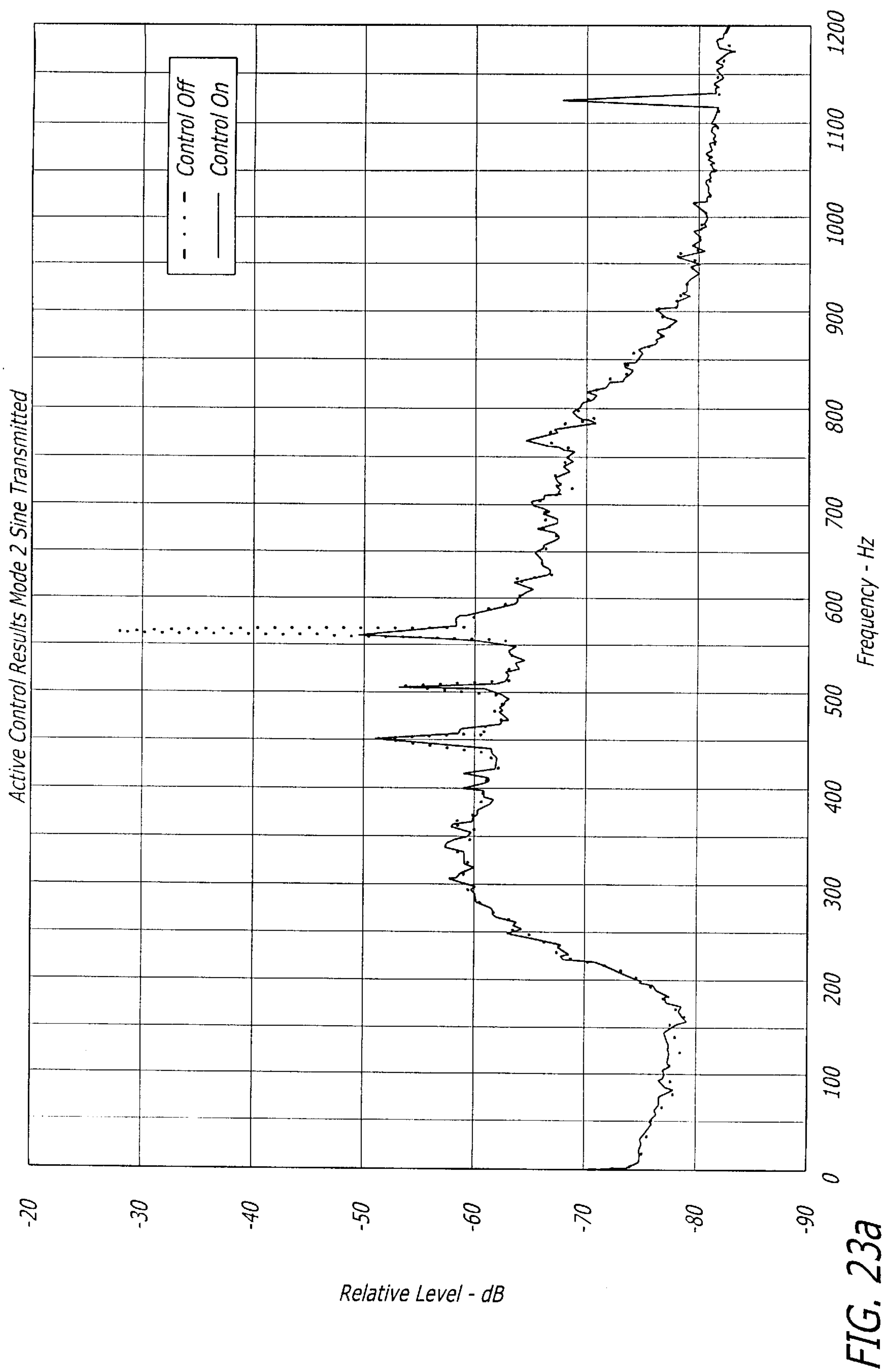
FIGS. 23(*a–d*) for the (2,0) mode show that well over 20 dB global absorption was achieved for the sine and cosine components of both modes using the test facility of FIG. 21.
Figure 23B:
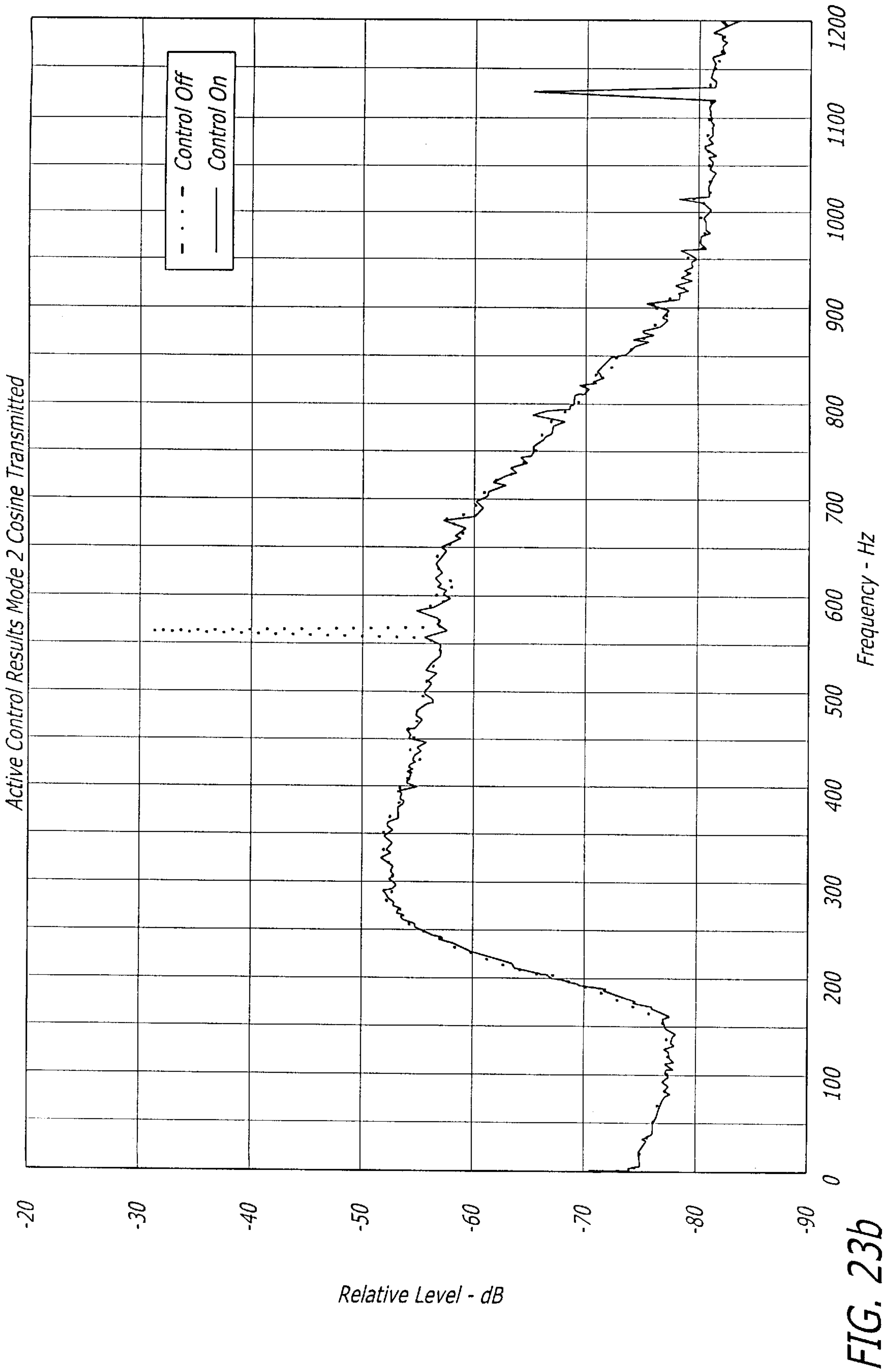
Figure 23C:
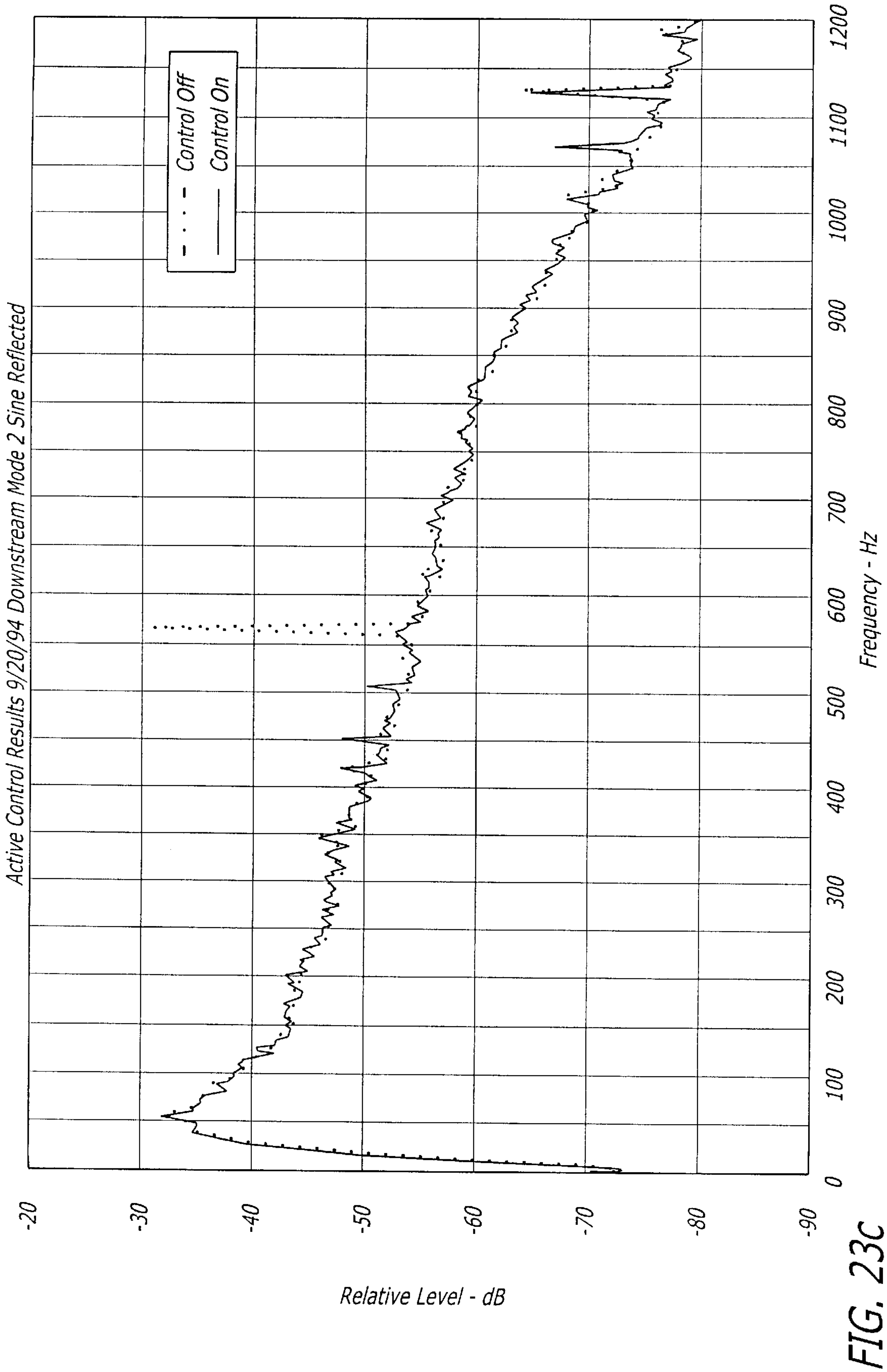
Figure 23D:
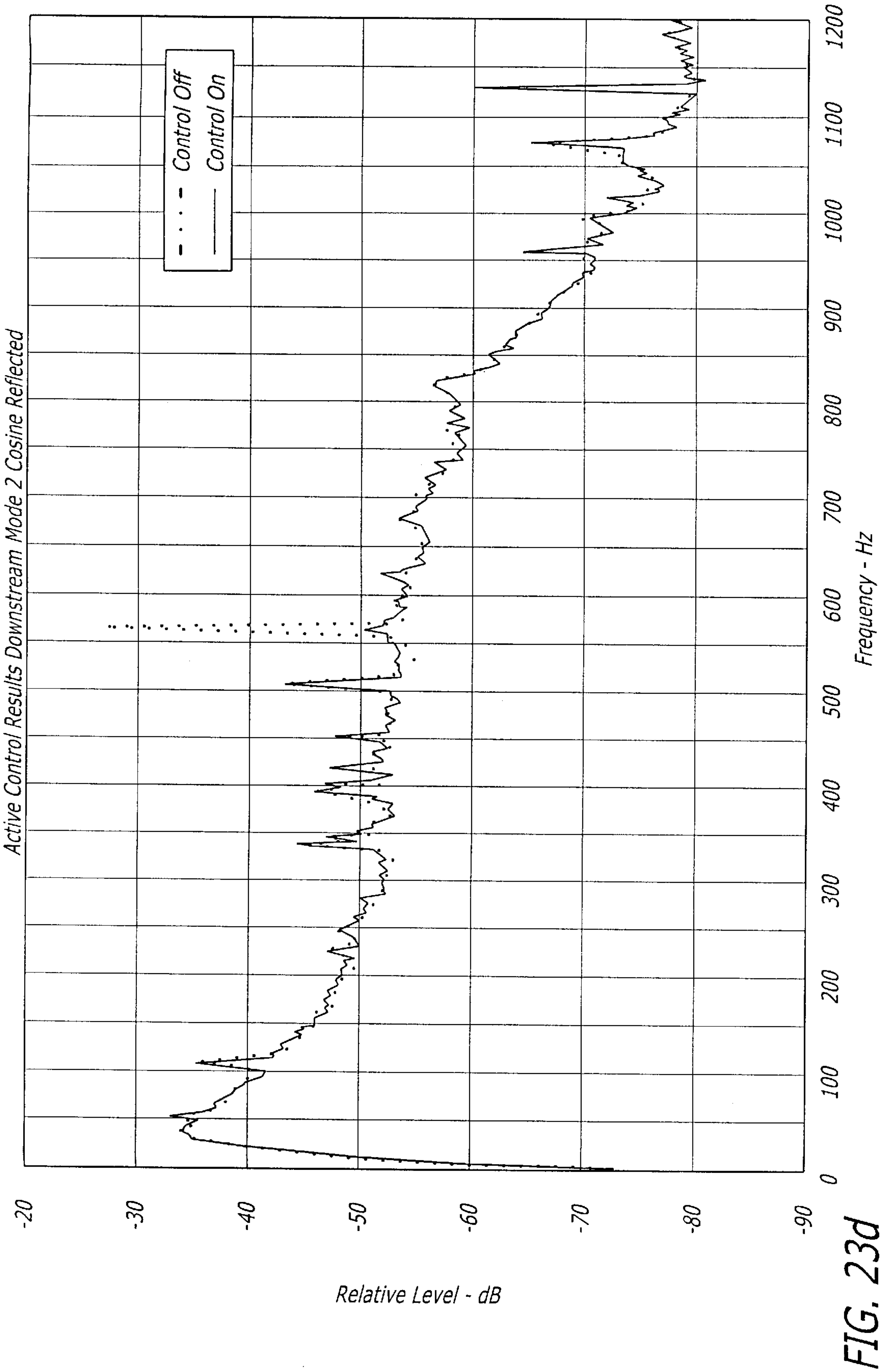

The dual source array technique shown in FIG. 21, for generating signals of arbitrary amplitude and phase relationship toward inlet and exhaust duct sections, may to adapted to a useful special case of radiation in one direction. The basic idea here was originally proposed by Swinbanks (*Active Control of Sound Waves,* Swinbanks, M. A., U.S. Pat. No. 4,044,204, Aug. 23, 1977) to globally cancel plane-wave sound in a duct. As shown by Swinbanks, if the two axially spaced source arrays are separated by $\Delta z$ less than ½ wavelength (¼ wavelength is optimal) and signal phases to the arrays are adjusted to $\pi - k_z\Delta z$, acoustical radiation will occur in one axial direction only. In other words, in an active control system, a controlled array can be constructed which radiates sound only in the direction of desired cancellation, effectively "absorbing" the unwanted noise. This results in two important advantages over the simple single controlled source approach: (1) feedback suppression if acoustic signal capture is used and (2) elimination of the "reflected" signal side effect of active control is achieved.

B. TEST RESULTS

FIGS. 22(*a–d*) for the (1,0) mode and FIGS. 23(*a–d*) for the (2,0) mode show that well over 20 dB global absorption was achieved for the sine and cosine components of both modes. Table V below summarizes the absorption achieved.

TABLE V

Active Resonator Global Absorption of (1,0) and (2,0) modes Absorption Achieved with Active Control Helmholtz Resonator Control System

| Mode | Direction | Component | Absorption - dB |
|---|---|---|---|
| 1,0 | Transmitted | Cosine | 25 |
| " | | Sine | 24 |
| " | Reflected | Cosine | 24 |
| " | | Sine | 23 |
| 2,0 | Transmitted | Cosine | 26 |
| " | | Sine | 22 |
| " | Reflected | Cosine | 23 |
| " | | Sine | 22 |

Passive Suppression of 2×BPF Tones

An experimental study was conducted to assess the capabilities of sizing the dimensions of the Helmholtz resonators so that their natural tuned frequency passively suppressed 2×BPF signals at mode 2,0. This investigation was conducted in the 24" diameter tube using the ten blade/eight stator Joy fan with nine upstream rods as a source.

The first part of the study was directed toward tuning the resonators to the desired frequency range of approximately 1100 Hz. For the resonators as used for the (1,0), (2,0) BPF attenuation described above, the response peak and impedance minimum agreed very closely. However, with the resonator volume reduced to that required for 1100 Hz resonance (2×BPF), the agreement was poor, and the resonant frequency was lower than expected due to the added effective volume of the transducer. It was determined that the transducer volume effect was too large to overcome; the passive resonator tests were undertaken by removing the transducers, reducing the resonator volumes to a computed resonance of 1100 Hz and capping the backs of the cavities.

Figure 24:
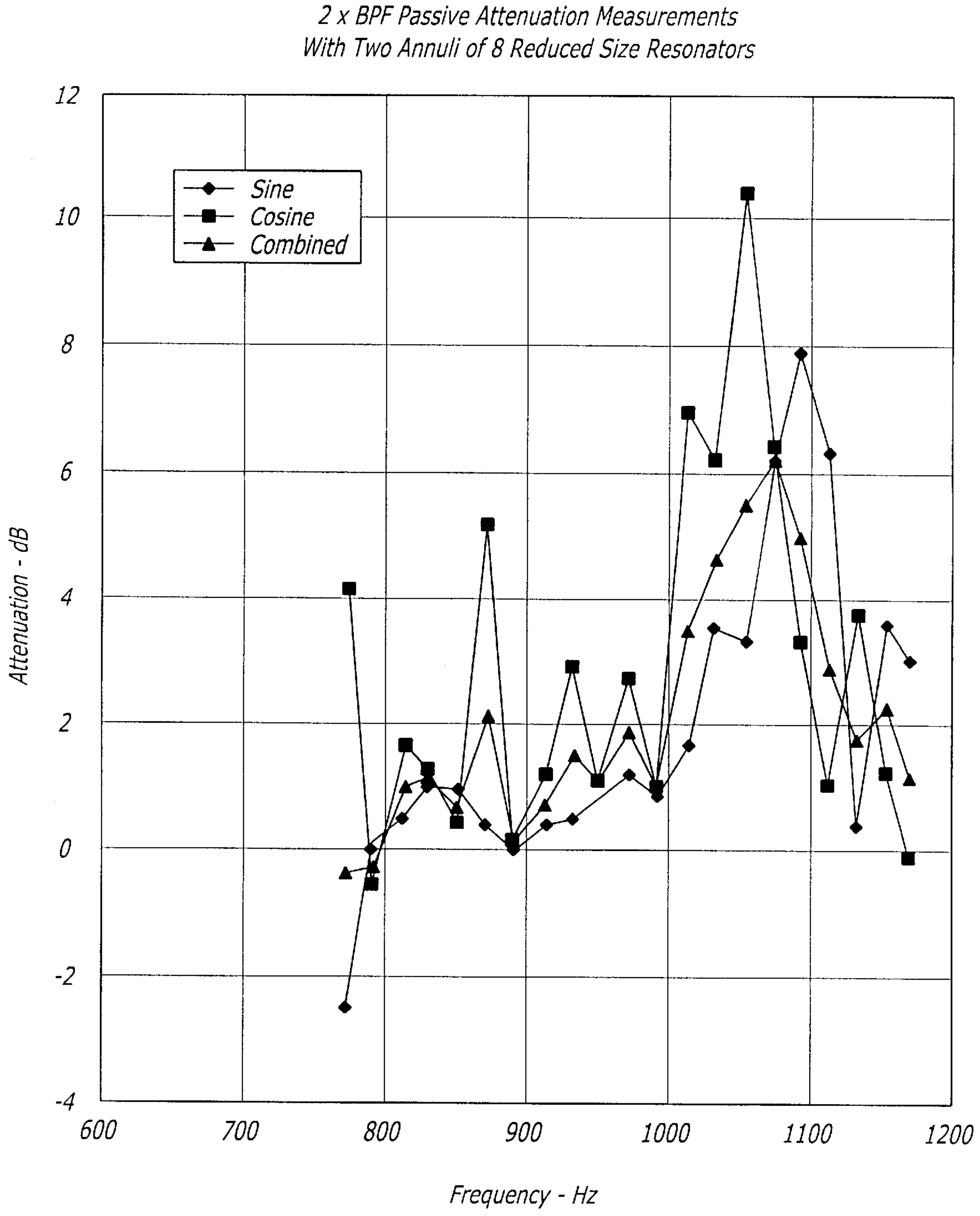
FIG. 24 shows measurements of passive attenuation by comparing the (2,0) mode 2×BPF signal levels on the downstream (incident) and upstream (transmitted) sides of the resonator array, using the mode separation matrices and wave direction separation techniques described in Section III. The comparison was made with the resonators exposed to the duct and with the orifices blocked.

Passive attenuation was measured by comparing the (2,0) mode 2×BPF signal levels on the downstream (incident) and upstream (transmitted) sides of the resonator array, using the mode separation matrices and wave direction separation techniques described in Section III. The comparison was made with the resonators exposed to the duct and with the orifices blocked. Measurement results are shown in FIG. 24. For the Sine component of the wave, the resonators resulted in 8 dB attenuation at a peak frequency 1090 Hz. For the Cosine component, the attenuation was 10.5 dB at 1050 Hz. The difference between the Sine and Cosine performance was discovered to be the result of additional openings in the faces of the Sine resonators; the cavity volume scaling computations were done for one of the Sine resonators. The combined overall attenuation was 6 dB at 1070 Hz, with a bandwidth of approximately 100 Hz, showing the effect that could be achieved with purposeful stagger tuning of the resonators. These test results indicate that active Helmholtz resonators can be designed to provide passive additional sound absorption of higher harmonic tones.

3. CONCLUDING REMARKS

There has been described herein methods and apparatus to substantially reduce selected modes of sound in the sound fields of cylindrical ducts excited by rotor/stator interactions in axial-flow fans. These forms of sound fields take the form of "spinning modes" with frequency an integer multiple of the number of rotor blades B times the rotational speed Ω and tangential wave number m as derived by Tyler-Sofrin. In accordance with one method, referred to herein as source cancellation, a first circumferential array of active sound sources is disposed just upstream of the stator guide vanes, and a second circumferential array of active sound sources is disposed just downstream of the stator guide vanes. Also first and second circumferential arrays of microphones are positioned in predetermined axial separation in the inlet duct upstream of the first array of active sound sources, and third and fourth circumferential arrays of microphones are positioned in predetermined axial separation in the outlet duct downstream of the second array of active sound sources. Preferably the number of sound sources and microphones (sound sensors) in each array exceeds the minimum number required for the detection and reduction of the selected modes so as to provide antialiasing of higher order modes not selected for reduction. Obviously, normally the most dominant modes would be selected for reduction, though lesser modes which are aliased because of insufficient number of devices in each array not only are themselves present, but decrease the reduction achievable in the selected modes.

The microphone signals from the two upstream arrays of microphones are used to detect the amplitude and phase of the selected modes of sound propagating in the upstream direction, separating the same from the amplitude and phase of the selected modes of sound propagating in the downstream direction. The microphone signals from the two downstream arrays of microphones are used to detect the amplitude and phase of the selected modes of sound propagating in the downstream direction, separating the same from the amplitude and phase of the selected modes of sound propagating in the upstream direction. Then the signals representing the sound propagating upstream and downstream from the stator vanes are mixed in an adaptive controller to provide the drive signals to the active sound sources to grossly reduce the amplitude of one or more modes of noise propagating upstream and downstream to the arrays of active sound sources.

Also disclosed is a sound absorption method and apparatus which uses a similar adaptive controller to absorb one or more modes of sound. In this method, for absorption of sound propagating upstream through the inlet duct from the axial fan, first and second circumferential arrays of active sound sources in the form of active Helmholtz resonators are disposed in the inlet duct upstream of the stator guide vanes, and first and second circumferential arrays of microphones are positioned in predetermined axial separation in the inlet duct upstream of the first and second arrays of active sound sources. Again preferably the number of sound sources and microphones (sound sensors) in each array exceeds the minimum number required for the detection and reduction of the selected modes so as to provide antialiasing of higher order modes not selected for reduction. As before, the microphone signals from the two upstream arrays of microphones are used to detect the amplitude and phase of the selected modes of sound propagating in the upstream direction, separating the same from the amplitude and phase of the selected modes of sound propagating in the downstream direction. Then the signals representing the sound propagating upstream from the stator vanes are mixed in the adaptive controller to provide the drive signals to the active sound sources to absorb most of one or more modes of noise propagating upstream to the arrays of active sound sources.

Two arrays of active sound sources are used upstream of the fixed stator vanes rather than only one, as two arrays, properly driven, can be made to absorb sound propagating thereto without generating any additional sound waves. A single array of active sound sources, on the other hand, could be used to generate equal and opposite waves to the selected waves generated by the rotor/stator blade interactions and traveling upstream to cancel the same from further propagation out the inlet, but this generates strong standing waves between the fan and the array of active sources. Proper spacing and phasing of the drive of the pair of active sound source arrays allows absorption without generating substantial standing waves between the active sound sources and the fan. In the embodiment of FIG. 21, two additional circumferential arrays of microphones are provided in the duct between the arrays of active sound sources and the fan. These arrays of microphones sense, and allow the separation of, the sound propagating from the fan to the arrays of active sound sources from the sound propagating down the duct from the arrays of active sound sources to the fan. This allows the adaptive adjustment of the amplitude and the phasing of the drive of the pair of active sound source arrays to minimize the standing waves between the active sound sources and the fan. The same arrangement of microphones and active sound sources may be used in the outlet duct to absorb one or more modes of noise therein also.

In certain applications, there may not be sufficient space adjacent the fan to use the source cancellation method and apparatus, in which case the sound absorption technique may be considered. In other applications, the sound absorption technique may not be appropriate because of the shortness of the ducts. In still other applications, both techniques may be used simultaneously, the sound absorption technique being used in one or both ducts, as desired, to further reduce one or more of the modes of sound selected for reduction using the source cancellation technique, and/or to reduce the sound in one or more modes not selected for reduction using the source cancellation technique.

Active Source Cancellation Invention

An adaptively controlled dipole sound source system has been tested and shown to provide 29 dB of attenuation in the inlet and 19 dB in the exhaust of the cosine component of the (2,0) rotor-stator interaction tone in an axial fan facility. The system is currently configured to cancel the cosine component of a single mode. It is straightforward to extend this system to globally cancel both the sine and cosine components simultaneously of a single mode as well as the global cancellation of M-modes. This would require an analog system to (1) generate each of the modes from a single sine wave using a multiple-source acoustic array and (2) monitor the microphone array to generate quadrature components for each of the M-modes. In the simplest arrangement in which rotor-stator propagating modes are generated using a linear combination of the mircophone signals, there is the implicit assumption of orthogonality of the modes. If this is not the case, the possibility arises of cross-talk between the mode-outputs. One of the major advantages of this scheme is that it will achieve global cancellation of multi-modal sound waves propagating at different frequencies. The scheme breaks down, however, for multi-modal sound waves propagating at the same frequency. Provided the analog hardware is available, the multi-mode system requires one control loop per mode. Each loop would require one output (to drive the analog mode generator) and two inputs for the quadrature components of the modes. In the case where the sum of upstream and downstream power needs to be minimized, there are four rather than two quadrature components per mode.

The novelty of the control scheme is that by utilizing knowledge of the mode transmitted in the duct, the complexity of the control algorithm is reduced dramatically. Furthermore, since the system is configured to only generate the desired mode, one can expect superior performance since unwanted plane-waves and other modes will not be generated.

Active Hemholtz Resonator Invention

An adaptively controlled Helmholtz resonator system has been tested and shown to achieve over 20 dB global absorption of the sine and cosine components of 1,0) and (2,0) BPF sound fields within the inlet of an axial fan. The method can be easily used to provide global absorption of sound energy in the inlet and exhaust section of axial fans.

What is claimed is:

1. An active-control system for attenuating noise in a duct having a fluid flow comprising:

an array of stators positioned axially within the duct having a longitudinal length;

a first array of sound sources capable of generating spinning mode sound and positioned a distance upstream of a first plane defined by the upstream-most portion of the stators, relative to the fluid flow, the upstream distance being less than the longitudinal length of the stators;

a second array of sound sources capable of generating spinning mode sound and positioned a distance downstream of a second plane defined by the downstream-most portion of the stators, relative to the fluid flow, the downstream distance being less than the longitudinal length of the stators; and a controller for causing the first and second arrays of sound sources to generate sound including spinning mode sound such that it cancels a portion of the noise within the fluid flow that passes through the stators.

2. The system described in claim 1 further comprising:

an axial fan positioned within the duct and having a plurality of rotors that generates the fluid flow; and a fan tachometer that measures the rotational speed of the axial fan, and where the fan tachometer sends a signal to the controller representative of the rotational speed of the axial fan;

wherein the controller causes the first and second arrays of sound sources to modify the sound they generate in accordance with the rotational speed of the axial fan to cancel a greater portion of the noise generated by the rotor-stator interaction of the fluid flow.

3. The system described in claim 1 further comprising a downstream array of sound-measuring devices positioned downstream of the second array of sound sources relative to the fluid flow, and where the downstream array of sound-measuring devices send a plurality of signals to the controller representative of the sound field in the duct measured by the downstream array of sound-measuring devices;

wherein the controller causes the first and second arrays of sound sources to modify the sound they generate to minimize the noise measured by the downstream array of sound-measuring devices.

4. The system described in claim 2 further comprising:

a downstream array of active-control components positioned downstream of the second array of sound sources, and upstream of the downstream sound-measuring devices relative to the fluid flow; and a sound-generating source in each downstream active-control component; and wherein the controller causes the downstream array of sound-generating sources to generate sound such that it attenuates a portion of the noise in the duct adjacent to the downstream array of active-control components.

5. The system described in claim 4 in which each of the downstream active-control components further comprises a resonator in which the sound-generating devices are housed, and in which the controller causes the downstream sound-generating devices to generate sound such that the various resonator cavities absorb a portion of the noise adjacent to the downstream array of active-control components.

6. The system described in claim 4 in which the downstream array of active-control components comprises a plurality of circumferential rows of downstream active-noise components.

7. The system described in claim 1 further comprising an upstream array of sound-measuring devices positioned upstream of the first array of sound devices relative to the fluid flow, and wherein the upstream array of sound-measuring devices sends a plurality of signals to the controller representative of the sound field in the duct measured by the upstream array of sound-measuring devices;

wherein the controller causes the first and second arrays of sound sources to modify the sound they generate to minimize the noise measured by the upstream array of sound-measuring devices.

8. The system described in claim 7 further comprising:

an upstream array of active-control components positioned upstream of the first array of sound sources, and downstream of the upstream sound-measuring devices relative to the fluid flow; and a sound-generating source in each upstream active-control component; and wherein the controller causes the upstream array of sound-generating sources to generate sound such that it attenuates a portion of the noise in the duct adjacent to the upstream array of active-control components.

9. The system described in claim 8 in which each of the upstream active-control components further comprises a resonator in which the sound-generating devices are housed, and in which the controller causes the upstream sound-generating devices to generate sound such that the various resonator cavities absorb a portion of the noise adjacent to the upstream array of active-control components.

10. The system described in claim 9 in which the upstream array of active-control components comprises a plurality of circumferential rows of upstream active-noise components.

11. The system described in claim 3 further comprising an upstream array of sound-measuring devices positioned upstream of the first array of sound sources relative to the fluid flow, and where the upstream array of sound-measuring devices sends a plurality of signals to the controller representative of the sound field in the duct measured by the upstream array of sound-measuring devices;

wherein the controller causes the first and second arrays of sound sources to modify the sound they generate to minimize the noise measured by the upstream array of sound-measuring devices.

12. The system described in claim 4 further comprising:

an upstream array of active-control components positioned upstream of the first array of sound sources, and downstream of the upstream sound-measuring devices relative to the fluid flow; and a sound-generating source in each upstream active-control component; and wherein the controller causes the upstream array of sound-generating sources to generate sound such that it attenuates a portion of the noise in the duct adjacent to the upstream array of active-control components.

13. The system described in claim 12 in which each of the upstream active-control components further comprises a resonator in which the sound-generating devices are housed, and in which the controller causes the upstream sound-generating devices to generate sound such that the various resonator cavities absorb a portion of the noise adjacent to the upstream array of active-control components.

14. The system described in claim 13 in which the upstream array of active-control components comprises a plurality of circumferential rows of upstream active-noise components.

15. The system described in claim 12 in which the upstream and downstream sound-measuring devices are microphones that are flush mounted to the interior surface of the duct.

16. The system described in claim 12 in which the first and second arrays of sound sources further comprise piezoelectric transducers.

17. The system described in claim 12 in which the system is within a jet engine.

* * * * *